US012433741B2

(12) United States Patent
Lee, IV et al.

(10) Patent No.: US 12,433,741 B2
(45) Date of Patent: Oct. 7, 2025

(54) HAPTIC MANAGEMENT FOR DELIVERY OF INTRAOCULAR IMPLANTS

(71) Applicant: Alcon Inc., Fribourg (CH)

(72) Inventors: Jestwin Edwin Lee, IV, Grandview, TX (US); Kathryn Jensen, Sugar Land, TX (US); Anubhav Chauhan, Benbrook, TX (US); Todd Taber, Keller, TX (US); Yinghui Wu, Cedar Hill, TX (US); Saumya Dilip Yadav, Arlington, TX (US)

( * ) Notice: Subject to any disclaimer, the term of this patent is extended or adjusted under 35 U.S.C. 154(b) by 804 days.

(21) Appl. No.: 17/457,278

(22) Filed: Dec. 2, 2021

(65) Prior Publication Data

US 2022/0175517 A1 Jun. 9, 2022

Related U.S. Application Data

(60) Provisional application No. 63/120,955, filed on Dec. 3, 2020.

(51) Int. Cl.
*A61F 2/16* (2006.01)

(52) U.S. Cl.
CPC ...... *A61F 2/167* (2013.01); *A61F 2002/1682* (2015.04); *A61F 2002/169051* (2015.04)

(58) Field of Classification Search
CPC .. A61F 2002/169051; A61F 2002/1682; A61F 2002/1681; A61F 2/1678; A61F 2/1675
See application file for complete search history.

(56) References Cited

U.S. PATENT DOCUMENTS

| | | | |
|---|---|---|---|
| 7,156,854 | B2 | 1/2007 | Brown et al. |
| 8,308,736 | B2 | 11/2012 | Boukhny et al. |
| 8,308,799 | B2 | 11/2012 | Chen et al. |
| 8,377,076 | B2 | 2/2013 | Downer et al. |
| 8,956,408 | B2 | 2/2015 | Smiley |
| 8,968,396 | B2 | 3/2015 | Matthews et al. |
| 9,480,555 | B2 | 11/2016 | Downer et al. |
| 9,610,155 | B2 | 4/2017 | Matthews |
| 9,693,858 | B2 | 7/2017 | Hildebrand et al. |
| 9,855,139 | B2 | 1/2018 | Matthews et al. |
| 10,172,706 | B2 | 1/2019 | Auld et al. |
| 10,195,020 | B2 | 2/2019 | Matthews |
| 10,568,735 | B2 | 2/2020 | Brown et al. |

(Continued)

FOREIGN PATENT DOCUMENTS

| | | |
|---|---|---|
| EP | 1800623 A1 | 6/2007 |
| EP | 1857076 B1 | 7/2010 |

(Continued)

*Primary Examiner* — Jerrah Edwards
*Assistant Examiner* — Kia Xiong White

(57) ABSTRACT

An apparatus for eye surgery may comprise a nozzle having a delivery lumen, an implant bay coupled to the nozzle, and an implant disposed in the implant bay. The implant may comprise an optic body, a leading haptic, and a trailing haptic. In some examples, the implant may be an intraocular lens. The apparatus may further comprise an actuator comprising a housing and a plunger disposed within the housing and a leading splay arm operable to splay the leading haptic within the implant bay. The plunger can be operable to advance the optic body from the implant bay to the delivery lumen after the leading splay arm straightens the leading haptic.

26 Claims, 23 Drawing Sheets

(56) References Cited

U.S. PATENT DOCUMENTS

| | | | |
|---|---|---|---|
| 10,588,780 B2 | 3/2020 | Van Noy et al. | |
| 11,039,953 B2 | 6/2021 | Balachandran | |
| 12,004,944 B2 | 6/2024 | Weston | |
| 2008/0097460 A1 | 4/2008 | Boukhny et al. | |
| 2008/0147081 A1 | 6/2008 | Pynson | |
| 2008/0221584 A1 | 9/2008 | Downer | |
| 2010/0057093 A1 | 3/2010 | Ide et al. | |
| 2011/0265779 A1 | 11/2011 | Vandrak et al. | |
| 2012/0022548 A1 | 1/2012 | Zacharias | |
| 2013/0197532 A1 | 8/2013 | Boukhny et al. | |
| 2013/0253527 A1 | 9/2013 | Schneider et al. | |
| 2014/0012277 A1* | 1/2014 | Matthews | A61F 2/167 606/107 |
| 2014/0257315 A1 | 9/2014 | Wu | |
| 2014/0276898 A1 | 9/2014 | Novak | |
| 2015/0238687 A1 | 8/2015 | Novakovic et al. | |
| 2015/0282928 A1* | 10/2015 | Auld | A61F 9/007 623/6.12 |
| 2016/0087460 A1 | 3/2016 | Rich et al. | |
| 2017/0007237 A1 | 1/2017 | Yates et al. | |
| 2017/0027686 A1 | 2/2017 | Nagasaka et al. | |
| 2017/0119522 A1 | 5/2017 | Auld et al. | |
| 2018/0049866 A1* | 2/2018 | Fayyaz | A61F 2/167 |
| 2018/0200046 A1 | 7/2018 | Brown et al. | |
| 2020/0179101 A1 | 6/2020 | Flowers et al. | |
| 2020/0179102 A1 | 6/2020 | Chen et al. | |
| 2020/0179103 A1 | 6/2020 | Auld et al. | |
| 2020/0188089 A1* | 6/2020 | Auld | A61F 2/167 |
| 2020/0197170 A1 | 6/2020 | Auld et al. | |
| 2021/0052371 A1* | 2/2021 | Singh | A61F 2/167 |
| 2022/0265420 A1 | 8/2022 | Kelp | |

FOREIGN PATENT DOCUMENTS

| | | | |
|---|---|---|---|
| EP | 3560457 | A1 | 10/2019 |
| JP | 2010063777 | B | 10/2013 |
| WO | 2014145562 | A1 | 9/2014 |
| WO | 2020065516 | A1 | 4/2020 |
| WO | 2020128762 | A1 | 6/2020 |
| WO | 2020151908 | A1 | 7/2020 |

* cited by examiner

HAPTIC MANAGEMENT FOR DELIVERY OF INTRAOCULAR IMPLANTS

PRIORITY CLAIM

This application claims the benefit of priority of U.S. Provisional Patent Application Ser. No. 63/120,955 titled "HAPTIC MANAGEMENT FOR DELIVERY OF INTRAOCULAR IMPLANTS," filed on Dec. 3, 2020, whose inventors are Jestwin Edwin Lee, IV, Kate Jensen, Anubhav Chauhan, Todd Taber, Yinghui Wu and Saumya Dilip Yadav, which is hereby incorporated by reference in its entirety as though fully and completely set forth herein.

TECHNICAL FIELD

The invention set forth in the appended claims relates generally to eye surgery. More particularly, but without limitation, the claimed subject matter relates to systems, apparatuses, and methods for inserting an implant into an eye.

BACKGROUND

The human eye can suffer a number of maladies causing mild deterioration to complete loss of vision. While contact lenses and eyeglasses can compensate for some ailments, ophthalmic surgery may be required for others. In some instances, implants may be beneficial or desirable. For example, an intraocular lens may replace a clouded natural lens within an eye to improve vision.

While the benefits of intraocular lenses and other implants are known, improvements to delivery systems, components, and processes continue to improve outcomes and benefit patients.

BRIEF SUMMARY

New and useful systems, apparatuses, and methods for eye surgery are set forth in the appended claims. Illustrative embodiments are also provided to enable a person skilled in the art to make and use the claimed subject matter.

For example, some embodiments may comprise or consist essentially of an apparatus for delivering an intraocular lens that includes at least one fixture configured to actively manipulate at least one haptic associated with the lens before delivery. In more particular embodiments, one or more fixtures can be configured to actively straighten a leading haptic, a trailing haptic, or both.

In some embodiments, a fixture may comprise a leading splay arm configured to actively straighten the leading haptic. For example, the leading splay arm can be advanced forward to engage and push the leading haptic forward to place it in a straightened orientation. In some embodiments, the leading splay arm may form a lower wall of a delivery channel. A plunger can then be used to engage the optic portion of the lens and advance the lens forward. As the plunger advances the lens, a second fixture can interact with the trailing haptic to passively straighten the trailing haptic. For example, the second fixture may comprise a portion of a side wall, which may be formed as a substantially rigid arm configured to engage the trailing haptic. In some embodiments, the leading splay arm and the plunger may be advanced forward together by a single actuator. In other embodiments, the leading splay arm and the plunger may be actuated independently.

Some embodiments may comprise two movable splay arms, each of which can engage with one of the haptics. The two arms may extend or move in opposite directions to orient, straighten, or otherwise manipulate the haptics. For example, one arm may move forward to straighten the leading haptic forward, and the other arm may move in the opposite direction to straighten the trailing haptic backward, resulting in a straight-straight haptic configuration suitable for delivery. In some examples, the arms may additionally form side walls, which can help retain the haptic configuration, prevent optic body rotation, or both. Side walls may also define a smaller lumen for maintaining alignment of the lens when it is advanced.

In some examples, the arms may be actuated by independent levers, dials, or similar features. Some embodiments may additionally, or alternatively, comprise a cam system configured to coordinate the actuation of the arms.

In some examples, two fixtures may be formed as part of inner walls of the delivery device for orienting the haptics prior to advancement. A first fixture may be in the form of an arm having a Y-shaped end for pushing or straightening the leading haptic. A second fixture may comprise a cam having a hook-shaped end, which can slide in an opposite direction to the first fixture to straighten the trailing haptic.

More generally, some embodiments of an apparatus for eye surgery may comprise a nozzle having a delivery lumen, an implant bay coupled to the nozzle, and an implant disposed in the implant bay. The implant may comprise an optic body, a leading haptic, and a trailing haptic. In some examples, the implant may be an intraocular lens. The apparatus may further comprise an actuator comprising a housing, a plunger disposed within the housing, and a leading splay arm operable to splay the leading haptic within the implant bay. The plunger can be operable to advance the optic body from the implant bay to the delivery lumen after the leading splay arm straightens the leading haptic.

In more particular embodiments, the implant bay may comprise a trailing splay arm operable to splay the trailing haptic of the lens. In some embodiments, the trailing splay arm may passively splay the trailing haptic as the plunger advances the lens. In other embodiments, the trailing splay arm may be actuated to actively splay the trailing haptic. For example, in some embodiments, the trailing splay arm may actively splay the trailing haptic before the plunger advances the lens. In some embodiments, the leading splay arm and the trailing splay arm may be operable to move in opposite directions.

Additionally, or alternatively, in some embodiments, the leading splay arm, the trailing splay arm, or both may form a wall adjacent to the optic body within the implant bay after splaying the leading haptic. In some embodiments, the leading splay arm, the trailing splay arm, or both, may comprise an end configured to facilitate engagement with the haptics. For example, various embodiments of the leading splay arm and the trailing splay arm may comprise notched ends, tapered ends, rounded ends, curved ends, or some combination thereof.

In some example embodiments, an apparatus for eye surgery may comprise an implant chamber and an implant disposed in the implant chamber. The implant may comprise an optic body, a leading haptic, and a trailing haptic. A leading splay arm may be operable to splay the leading haptic, and a trailing splay arm may be operable to splay the trailing haptic.

In more particular examples, the implant chamber may comprise a delivery port, the leading splay arm may be operable to move a free end of the leading haptic toward the delivery port, and the trailing splay arm may be operable to move a free end of the trailing haptic away from the delivery port. Some embodiments may additionally comprise a cam configured to translate the leading splay arm and the trailing splay arm.

Methods of ejecting a lens from a surgical delivery system may comprise providing the lens in an implant bay, straightening a leading haptic of the lens with a leading splay arm, advancing the lens from the implant bay to a delivery lumen with a rigid plunger, fluidly coupling a fluid chamber to a bore in the rigid plunger through a bypass channel, pressing fluid in the fluid chamber to move the fluid through the bypass channel and the bore to the delivery lumen, and advancing the lens through the delivery lumen with the fluid.

Features, elements, and aspects described in the context of some embodiments may also be omitted, combined, or replaced by alternative features. Other features, objectives, advantages, and a preferred mode of making and using the claimed subject matter are described in greater detail below with reference to the accompanying drawings of illustrative embodiments.

BRIEF DESCRIPTION OF THE DRAWINGS

The accompanying drawings illustrate some objectives, advantages, and a preferred mode of making and using some embodiments of the claimed subject matter. Like reference numbers represent like parts in the examples.

DESCRIPTION OF EXAMPLE EMBODIMENTS

The following description of example embodiments provides information that enables a person skilled in the art to make and use the subject matter set forth in the appended claims, but it may omit certain details already well known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive an implant. However, as should be recognized by those skilled in the art, this frame of reference is merely a descriptive expedient rather than a strict prescription.

Figure 1:
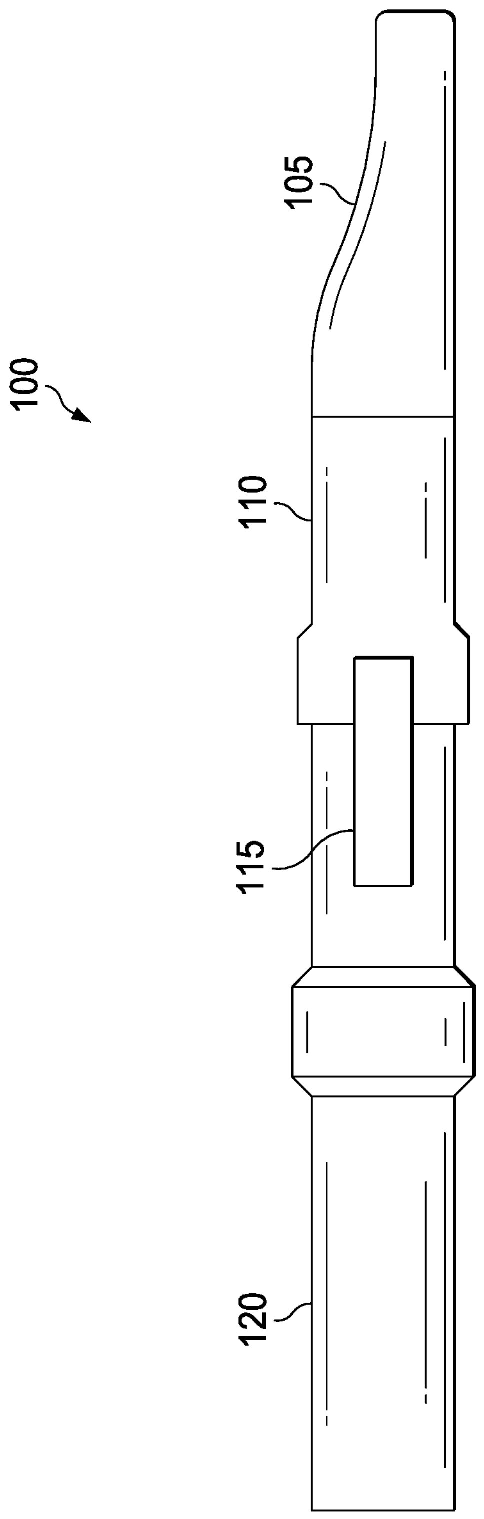
FIG. 1 is a schematic view of an example system for inserting an implant into an eye.

FIG. 1 is a schematic diagram of a system 100 that can insert an implant into an eye. In some embodiments, the system 100 may comprise two or more modules, which can be configured to be coupled and decoupled as appropriate for storage, assembly, use, and disposal. For example, as illustrated in FIG. 1, some embodiments of the system 100 may include a nozzle 105, an implant bay 110 coupled to the nozzle 105, and an actuator 115 coupled to the implant bay 110. In some embodiments, the system 100 may additionally comprise a drive module 120 configured to engage the actuator 115.

The nozzle 105 generally comprises a tip adapted for insertion through an incision into an eye. The size of the tip may be adapted to surgical requirements and techniques as needed. For example, small incisions are generally preferable to reduce or minimize healing times. Incisions of less than 3 millimeters may be preferable in some instances, and the tip of the nozzle 105 may have a width of less than 3 millimeters in some embodiments.

The implant bay 110 generally represents a wide variety of apparatuses that are suitable for storing an implant prior to delivery into an eye. In some embodiments, the implant bay 110 may additionally or alternatively be configured to prepare an implant for delivery. For example, some embodiments of the implant bay 110 may be configured to be actuated by a surgeon or other operator to prepare an implant for delivery by subsequent action of the actuator 115. In some instances, the implant bay 110 may be configured to actively deform, elongate, extend, or otherwise manipulate features of the implant before the implant is advanced into the nozzle 105. For example, the implant bay 110 may be configured to extend or splay one or more features, such as haptics, of an intraocular lens.

The actuator 115 is generally configured to advance an implant from the implant bay 110 into the nozzle 105, and thereafter from the nozzle 105 through an incision and into an eye.

The drive module 120 is generally operable to energize the actuator 115. In some examples, the drive module 120 may be operated by electrical, mechanical, hydraulic, or pneumatic power, or combinations thereof, or in some other manner. In some instances, the drive module 120 may be operated manually. According to other implementations, the drive module 120 may be an automated system.

In general, components of the system 100 may be coupled directly or indirectly. For example, the nozzle 105 may be directly coupled to the implant bay 110 and may be indirectly coupled to the actuator 115 through the implant bay 110. Coupling may include fluid, mechanical, thermal, electrical, or chemical coupling (such as a chemical bond), or some combination of coupling in some contexts. For example, the actuator 115 may be mechanically coupled to the drive module 120 and may be mechanically and fluidly coupled to the implant bay 110. In some embodiments, components may also be coupled by virtue of physical proximity, being integral to a single structure, or being formed from the same piece of material.

Figure 2:
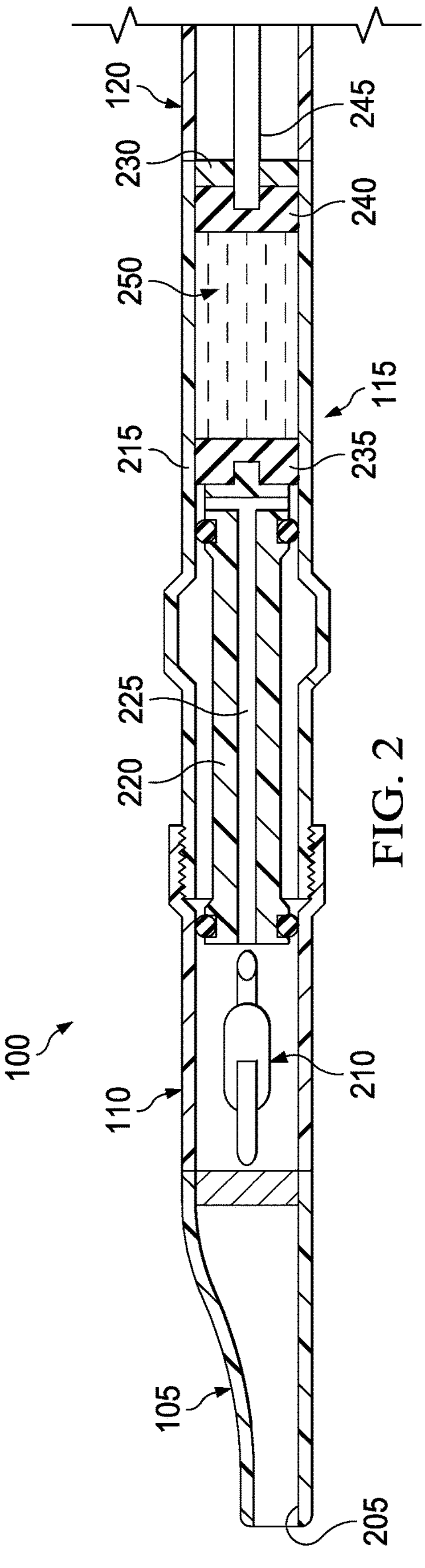
FIG. 2 is a schematic diagram of an example of the system of FIG. 1.

FIG. 2 is a schematic diagram of an example of the system 100, illustrating additional details that may be associated with some embodiments. In the example of FIG. 2, the nozzle 105 has a delivery lumen 205, and an implant 210 is disposed within the implant bay 110.

The actuator 115 of FIG. 2 generally comprises a housing 215, a plunger 220 disposed within the housing 215, a bore 225 through the plunger 220, and a drive interface 230 configured to couple with the drive module 120. The plunger 220 is generally comprised of a substantially rigid material, such as a medical grade polymer material. A plunger seal 235 may be disposed within the housing 215 and coupled to the plunger 220. A drive seal 240 may also be disposed within the housing 215. In some embodiments, the drive module 120 may comprise a push rod 245 configured to engage the drive seal 240 through the drive interface 230. For example, the drive interface 230 may comprise an aperture configured to receive the push rod 245.

As illustrated in the example of FIG. 2, the drive seal 240 may be disposed between the plunger seal 235 and the drive interface 230, and a fluid chamber 250 may be defined within the housing 215 between the plunger seal 235 and the drive seal 240. In the example configuration of FIG. 2, the plunger seal 235 is configured to provide a fluid seal across the housing 215 and substantially prevent movement of fluid from the fluid chamber 250 to the bore 225. The drive seal 240 may also be configured to provide a fluid seal across the housing 215 and substantially prevent movement of fluid from the fluid chamber 250 to the drive interface 230.

Figure 3:
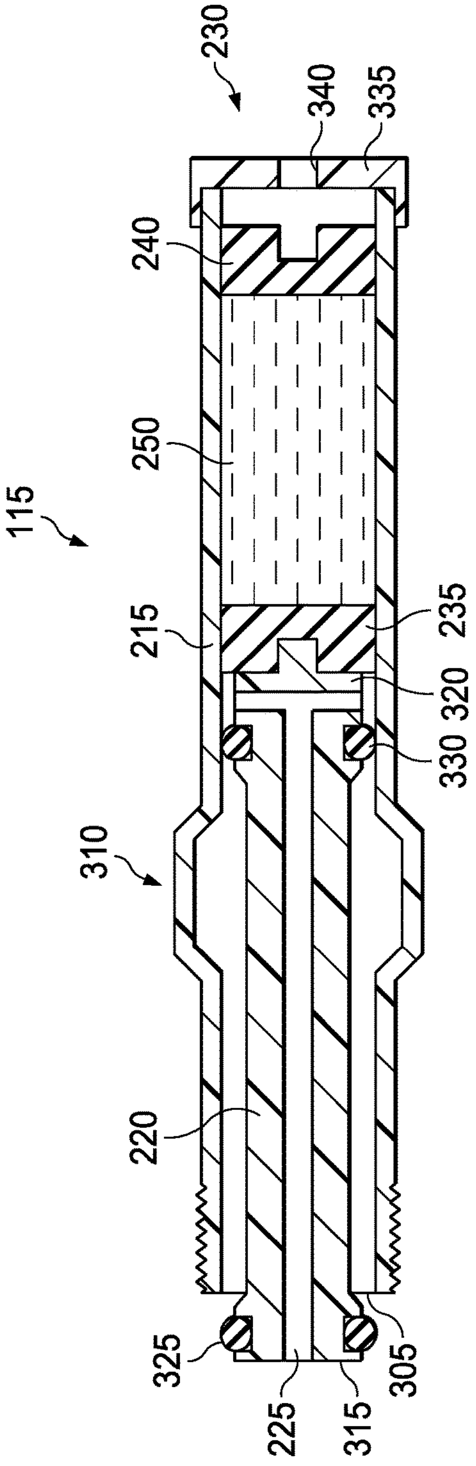
FIG. 3 is a detail view of an actuator that may be associated with the system of FIG. 2.

FIG. 3 is a detail view of the actuator 115 of FIG. 2, illustrating additional details that may be associated with some embodiments. For example, the housing 215 of FIG. 3 further comprises a plunger interface 305 and a bypass channel 310 disposed between the plunger interface 305 and the drive interface 230. The bypass channel 310 may take various forms. For example, the bypass channel 310 may comprise a protrusion in the housing 215, as illustrated in FIG. 3. In other examples, the bypass channel 310 may comprise a groove or recess in the inner surface of the housing 215. In some embodiments, the bypass channel 310 may comprise a plurality of channels. For example, a plurality of channels may be disposed circumferentially around the housing 215 in some embodiments.

The plunger 220 generally has a first end 315 and a second end 320, wherein the first end 315 is generally disposed adjacent to the plunger interface 305. The bore 225 generally passes through the plunger 220 longitudinally from the first end 315 to the second end 320.

In some embodiments, the actuator 115 may additionally comprise a nozzle seal 325 and a bypass seal 330. Each of the nozzle seal 325 and the bypass seal 330 are generally configured to create a seal between a portion of the plunger 220 and the housing 215 to substantially prevent movement of fluid past the seal. As illustrated in the example of FIG. 3, one or both of the nozzle seal 325 and the bypass seal 330 may be ring seals, such as an O-ring, disposed circumferentially around a portion of the plunger 220. In other examples, an umbrella seal may be suitable. In more particular embodiments, the nozzle seal 325 may be disposed proximate to the first end 315 of the plunger 220, and the bypass seal 330 may be disposed proximate to the second end 320 of the plunger 220.

The drive interface 230 of FIG. 3 comprises a cap 335 and an aperture 340. The cap 335 may be coupled to an end of the housing 215 to retain the drive seal 240 and other components within the housing 215.

Figure 4:
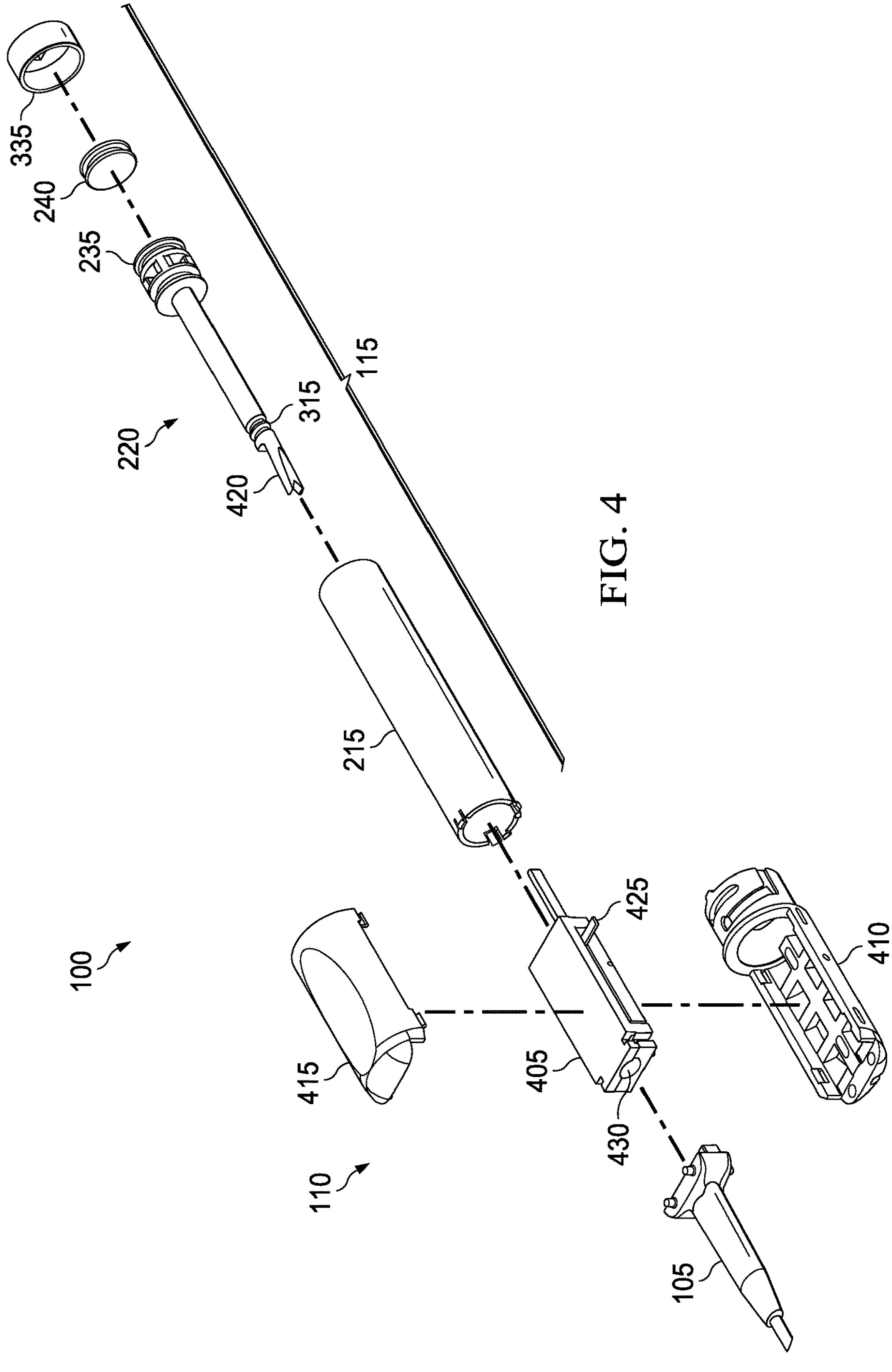
FIG. 4 is an assembly view of another example of the system of FIG. 1.

FIG. 4 is an assembly view of another example of the system 100. As illustrated in the example of FIG. 4, the implant bay 110 may comprise an implant management system 405, a carrier 410, and a cover 415. In various embodiments, the implant management system 405 can be any of a wide variety of systems, devices, components, or cartridges that are configured to prepare an implant for delivery. The carrier 410 and the cover 415 may be configured to substantially enclose the implant management system 405. The carrier 410 and the cover 415 may also be configured to be mechanically coupled to the nozzle 105 and to the actuator 115.

The housing 215 of FIG. 4 comprises a hollow cylinder, which can receive the plunger 220, the plunger seal 235, and the drive seal 240. FIG. 4 also illustrates an example of an implant interface 420, which may be coupled to the first end 315 of the plunger 220 in some embodiments. In the example of FIG. 4, the plunger 220 and the plunger seal 235 may be inserted into the housing 215, and then a suitable working fluid may be added before inserting the drive seal 240 and attaching the cap 335 to the housing 215.

In some examples, an implant (not shown) may be preloaded into the implant management system 405. The implant management system 405 is generally configured to store and manipulate an implant. For example, some embodiments of the implant management system 405 may be configured to orient or fold an implant. In some instances, the implant management system 405 may be configured to fold, splay, or straighten haptics of an intraocular lens. In the example of FIG. 4, the implant management system 405 comprises a leading splay arm 425, which may be operable to manipulate an implant within an implant chamber 430 of the implant management system 405. Other examples may additionally or alternatively comprise other suitable mechanisms for manipulating the leading splay arm 425, such as a rotating dial, cap, or wheel. In the example of FIG. 4, the leading splay arm 425 is configured to accept a manual actuation of the implant management system 405.

Figure 5:
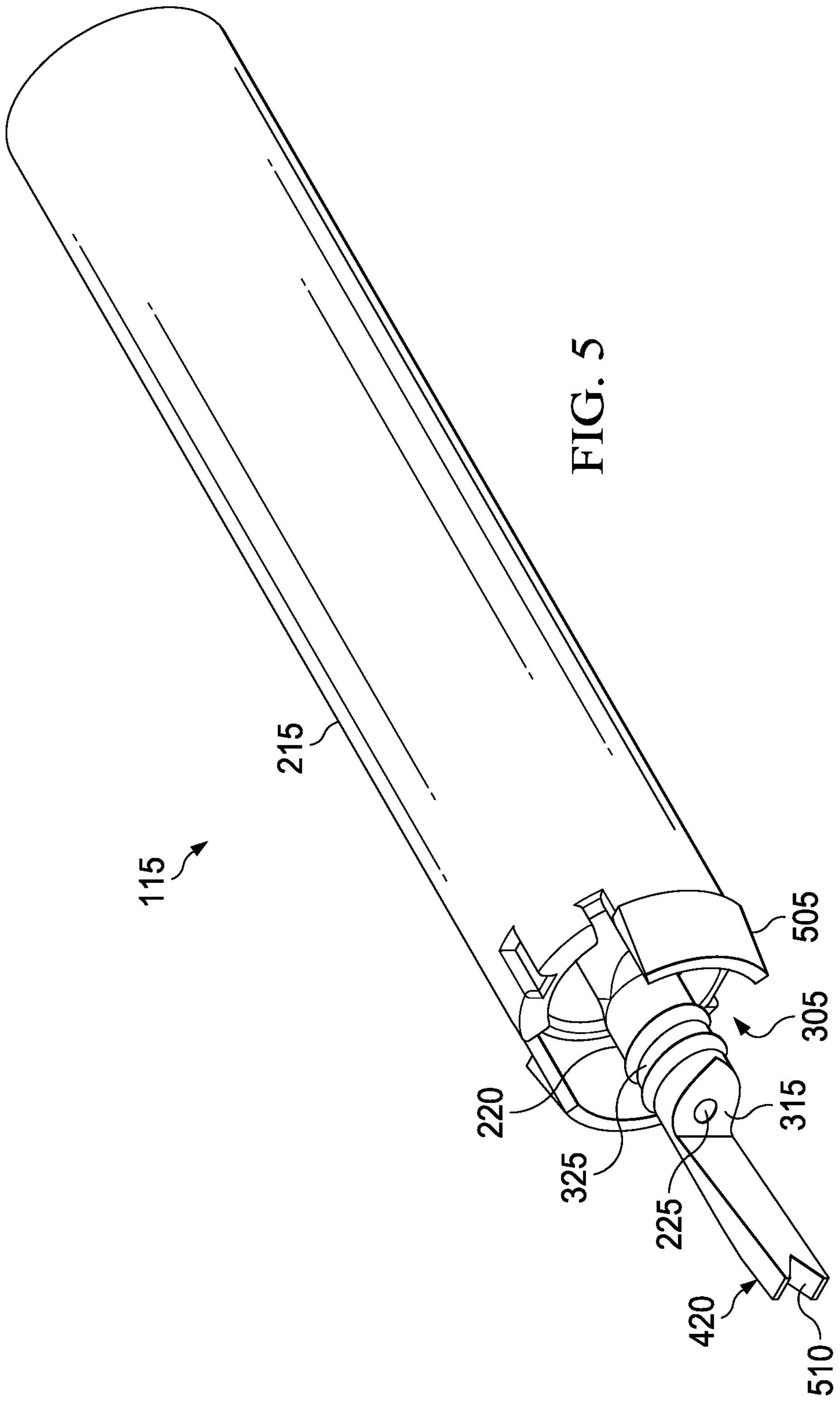
FIG. 5 is a detail view of an actuator illustrated in FIG. 4.

FIG. 5 is an isometric view of the actuator 115 of FIG. 4, as assembled. As illustrated in the example of FIG. 5, some embodiments of the plunger interface 305 may comprise an opening in the housing 215 and one or more locking tabs 505. The implant interface 420 and at least a portion of the plunger 220 may extend through the plunger interface 305. The nozzle seal 325 of FIG. 5 comprises an O-ring disposed around the plunger 220 adjacent to the first end 315. As seen in the example of FIG. 5, the bore 225 may define an opening in the first end 315. In some embodiments, the opening may be centrally disposed through the first end 315, and the implant interface 420 may be coupled to the plunger 220 adjacent to the opening in the first end 315. The implant interface 420 may comprise a notch 510, which may be configured to engage an implant.

Figure 6:
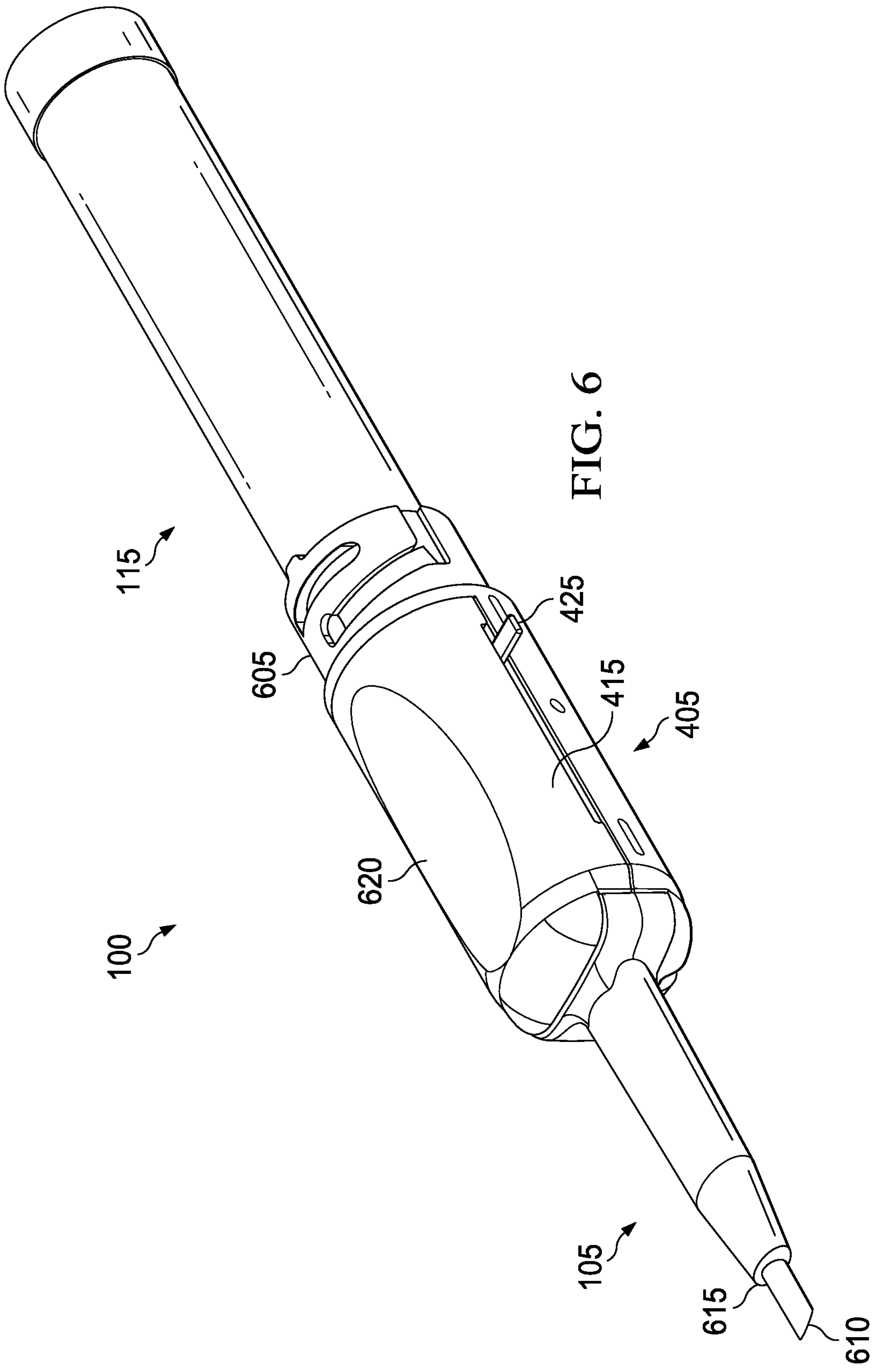
FIG. 6 is an isometric view of the system of FIG. 4, as assembled.

FIG. 6 is an isometric view of the system 100 of FIG. 4 as assembled, illustrating additional details that may be associated with some embodiments. As illustrated in the example of FIG. 6, the system 100 may have a slender, elongated shape. In some instances, the actuator 115 may be at least partially inserted into the implant bay 110 and secured in position by a locking mechanism 605 adapted to engage interlocking features of the actuator 115, such as the locking tabs 505. In other examples, the actuator 115 may be secured by other suitable fasteners, interference fit, or thermal or chemical bonding.

As illustrated in the example of FIG. 6, some embodiments of the nozzle 105 may comprise an insertion tip 610 and a depth guard 615. The insertion tip 610 may be adapted to minimize shear forces on an incision. In some examples, the insertion tip 610 may be beveled or angled. The depth guard 615 may comprise a flared portion adapted to contact the eye around the incision to limit the penetration depth of the insertion tip 610.

Some embodiments of the system 100 may additionally include various ergonomic features. In FIG. 6, for example, the cover 415 of the implant bay 110 includes a relief 620. The relief 620 of FIG. 6 comprises a shallow recess formed in the cover 415 to accommodate, for example, one or more fingers of an operator. The relief 620 may additionally include a textured surface that may improve grip of and control over the system 100.

Figure 7:
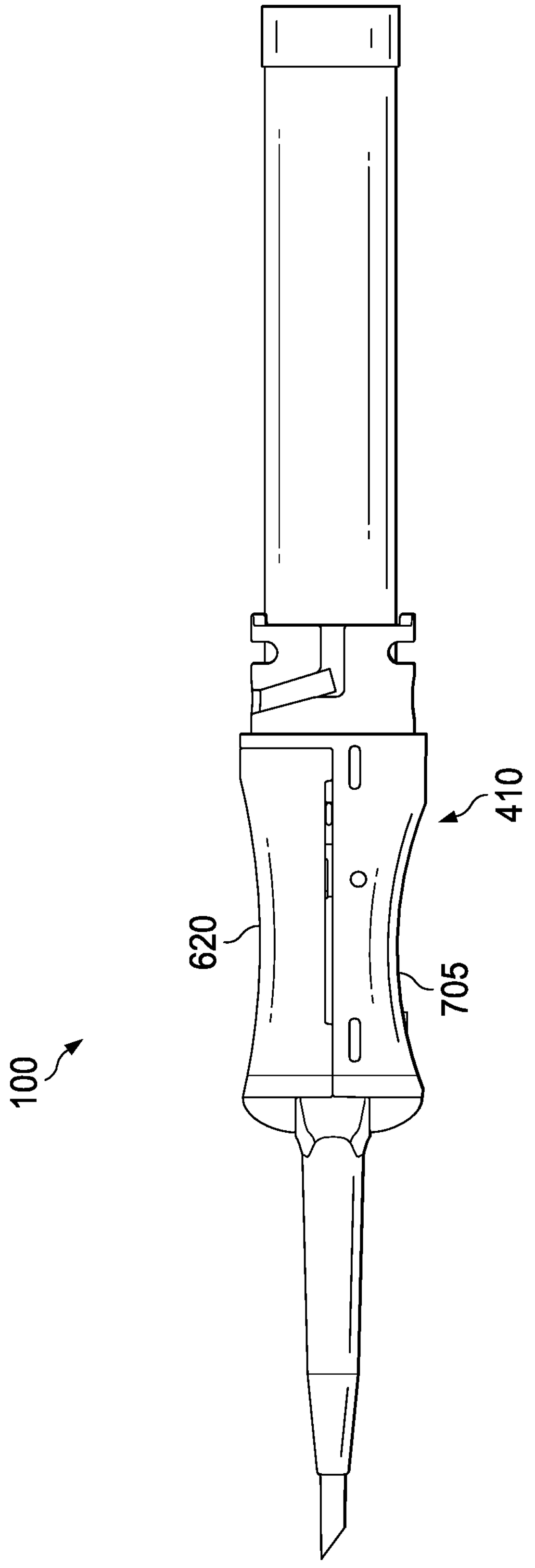
FIG. 7 is a side view of the system of FIG. 6.

FIG. 7 is a side view of the system 100 of FIG. 6, illustrating additional details that may be associated with some embodiments. As illustrated in the example of FIG. 7, the carrier 410 may comprise a relief 705, similar or analogous to the relief 620.

Figure 8:
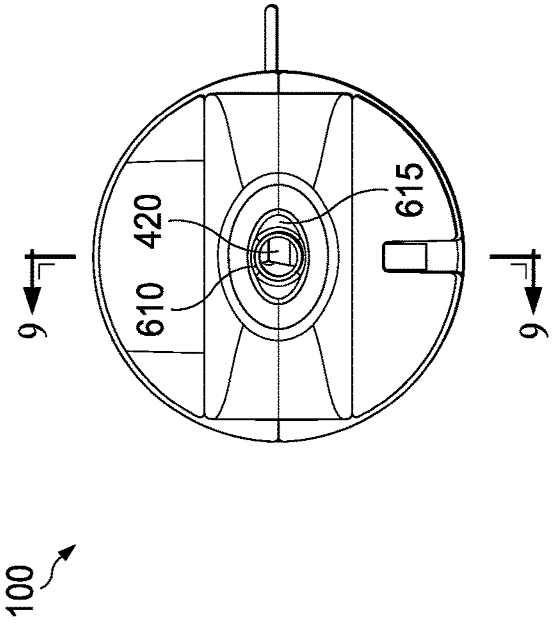
FIG. 8 is a front view of the system of FIG. 6.

FIG. 8 is a front view of the system 100 of FIG. 6. As illustrated in FIG. 8, the insertion tip 610 may have a circular profile, and the depth guard 615 may have an elliptical profile. The insertion tip 610 and the depth guard 615 may be concentric in some embodiments, as illustrated in the example of FIG. 8.

Figure 9:
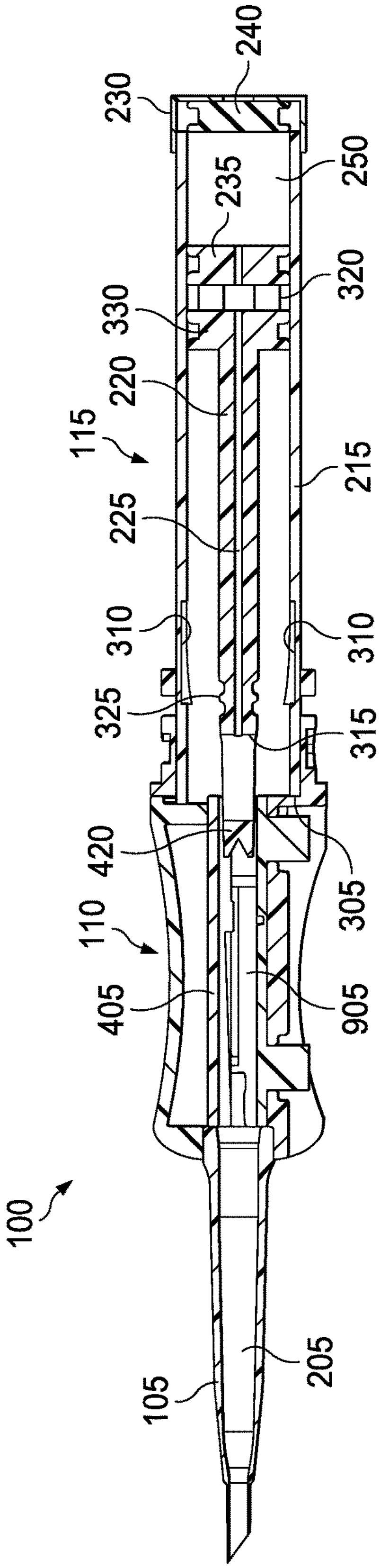
FIG. 9 is a section view of the system of FIG. 8.

FIG. 9 is a section view of the system 100 of FIG. 8 taken along line 9-9, illustrating additional details that may be associated with some embodiments. In the example of FIG. 9, the nozzle 105 is coupled to the implant bay 110, and the actuator 115 is coupled to the implant bay 110. The plunger 220 is disposed within the housing 215, and the bore 225 extends through the plunger 220 between the first end 315 and the second end 320. The plunger seal 235 may be disposed within the housing 215 and coupled to the second end 320 of the plunger 220.

The drive seal 240 may be disposed between the plunger seal 235 and the drive interface 230, and the fluid chamber 250 may be defined within the housing 215 between the plunger seal 235 and the drive seal 240. In the example configuration of FIG. 9, the plunger seal 235 is configured to provide a fluid seal across the housing 215 and substantially prevent movement of fluid from the fluid chamber 250 to the bore 225. The drive seal 240 may also be configured to provide a fluid seal across the housing 215 and substantially prevent movement of fluid from the fluid chamber 250 to the drive interface 230.

The bypass channel 310 may be disposed between the plunger interface 305 and the drive interface 230. The bypass channel 310 of FIG. 9 comprises a recess in the inner surface of the housing 215.

As illustrated in FIG. 9, some embodiments of the implant management system 405 may include an implant chamber 905, which can provide a fluid path between the bore 225 and the delivery lumen 205. The implant chamber 905 may also be configured to receive a portion of the plunger 220, including the implant interface 420 in some embodiments.

The example configuration of FIG. 9 is generally suitable for storing an implant (not shown) before delivery. More particularly, an implant may be stored in the implant chamber 905. The plunger seal 235, and the drive seal 240 can be disposed in a first position, wherein the plunger seal 235 fluidly isolates the bore 225 and the bypass channel 310 from the fluid chamber 250, allowing a suitable working fluid to be stored in the fluid chamber 250. Suitable working fluids may include, without limitation, a liquid, such as saline, or a viscous lubricant with non-Newtonian properties.

Figure 10:
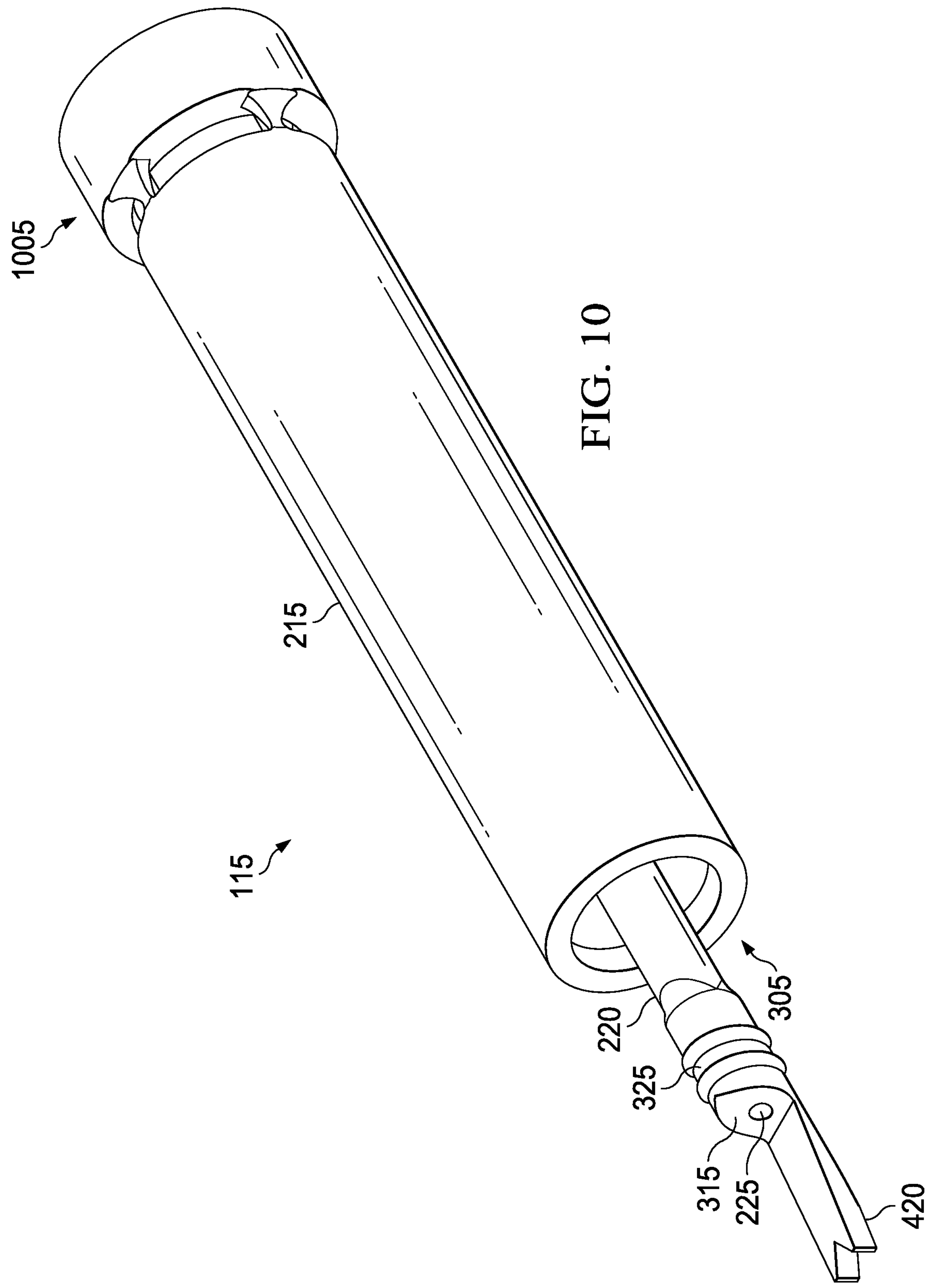
FIG. 10 is an isometric view of another example of an actuator that may be associated with the system of FIG. 1.

FIG. 10 is an isometric view of another example of the actuator 115, illustrating additional details that may be associated with some embodiments. The actuator 115 of FIG. 10 is similar to the actuator 115 of FIG. 5. For example, the plunger interface 305 of FIG. 10 may comprise an opening in the housing 215, and the implant interface 420 and at least a portion of the plunger 220 may extend through the plunger interface 305. The nozzle seal 325 of FIG. 10 comprises an O-ring disposed around the plunger 220 adjacent to the first end 315. As seen in the example of FIG. 10, the bore 225 may define an opening in the first end 315. In some embodiments, the opening may be centrally disposed through the first end 315, and the implant interface 420 may be coupled to the plunger 220 adjacent to the opening in the first end 315. The actuator 115 of FIG. 10 further comprises a fluid fitting 1005.

Figure 11:
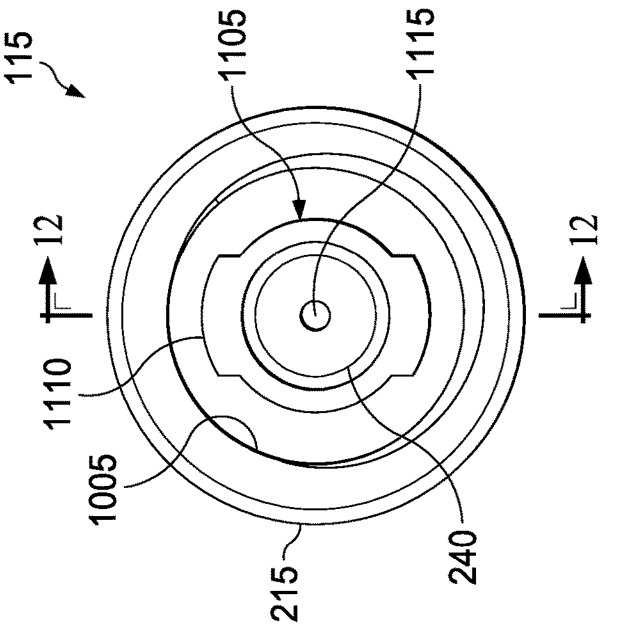
FIG. 11 is a rear view of the actuator of FIG. 10.

FIG. 11 is a rear view of the actuator 115 of FIG. 10, illustrating additional details that may be associated with some embodiments of the fluid fitting 1005. In the example of FIG. 11, at least a portion of the fluid fitting 1005 may be integral with the housing 215. The fluid fitting 1005 may be a luer lock, luer slip, or similar fitting configured to receive a syringe or other apparatus. For example, the fluid fitting 1005 of FIG. 11 comprises a female luer lock 1105 having at least one locking tab 1110 configured to engage threads on a compatible male luer lock fitting. A port 1115 may be disposed in the drive seal 240 of the female luer lock 1105.

Figure 12:
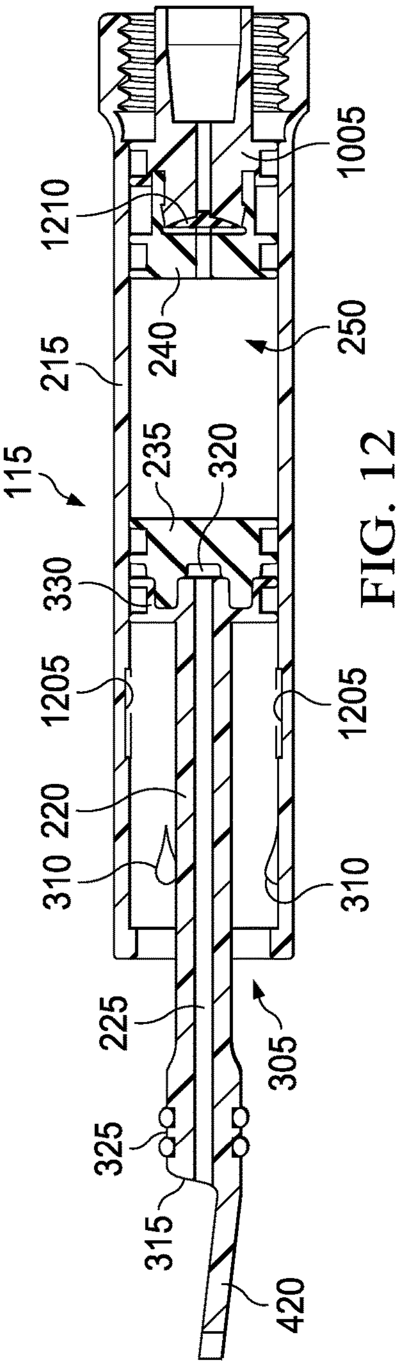
FIG. 12 is a section view of the actuator of FIG. 11.

FIG. 12 is a section view of the actuator 115 of FIG. 11 taken along line 12-12. In the example of FIG. 12, the plunger 220 is disposed within the housing 215, and the bore 225 extends through the plunger 220 between the first end 315 and the second end 320. The plunger seal 235 may be disposed within the housing 215 and coupled to the second end 320 of the plunger 220. The implant interface 420 may be coupled to the first end 315 in some embodiments of the plunger 220.

The drive seal 240 may be integral to or coupled to the fluid fitting 1005, and the fluid chamber 250 may be defined within the housing 215 between the plunger seal 235 and the drive seal 240. In the example configuration of FIG. 12, the plunger seal 235 is configured to provide a fluid seal across the housing 215 and substantially prevent movement of fluid between the bore 225 and the fluid chamber 250. The drive seal 240 may also be configured to provide a fluid seal across the housing 215 and substantially prevent movement of fluid between the drive interface 230 and the fluid chamber 250.

The bypass channel 310 may be disposed between the plunger interface 305 and the drive seal 240. In more particular embodiments, the bypass channel 310 may be disposed between the plunger interface 305 and the plunger seal 235. The bypass channel 310 of FIG. 12 comprises a recess in the inner surface of the housing 215. In some examples, the bypass channel 310 may have a width that that increases with distance from the plunger seal 235.

As illustrated in the example of FIG. 12, some embodiments of the actuator 115 may optionally have at least one priming channel 1205. The priming channel 1205 may take various forms. For example, the priming channel 1205 may comprise a groove or recess in the inner surface of the housing 215, as illustrated in the example of FIG. 12. In other examples, the priming channel 1205 may comprise a protrusion in the housing 215. In some embodiments, the priming channel 1205 may comprise a plurality of channels. For example, a plurality of channels may be disposed circumferentially around the housing 215 in some embodiments.

In the example of FIG. 12, the nozzle seal 325 is disposed proximate to the first end 315 of the plunger 220, and the bypass seal 330 is disposed proximate to the second end 320 of the plunger 220.

As illustrated in FIG. 12, the port 1115 may comprise a fill seal 1210. The fill seal 1210 may comprise a self-sealing material adapted to allow penetration of a fluid while sealing upon removal. For example, the actuator 115 of FIG. 12 may be transported and stored without fluid in the fluid chamber 250. A syringe or other suitable fluid source (not shown) may then be coupled to the fluid fitting 1105 through the port 1115 and the fill seal 1210 to add a suitable working fluid to the fluid chamber 250. Additionally, or alternatively, a check valve or umbrella valve may be configured to allow fluid to pass into the fluid chamber 250 and prevent backflow.

Figure 13:
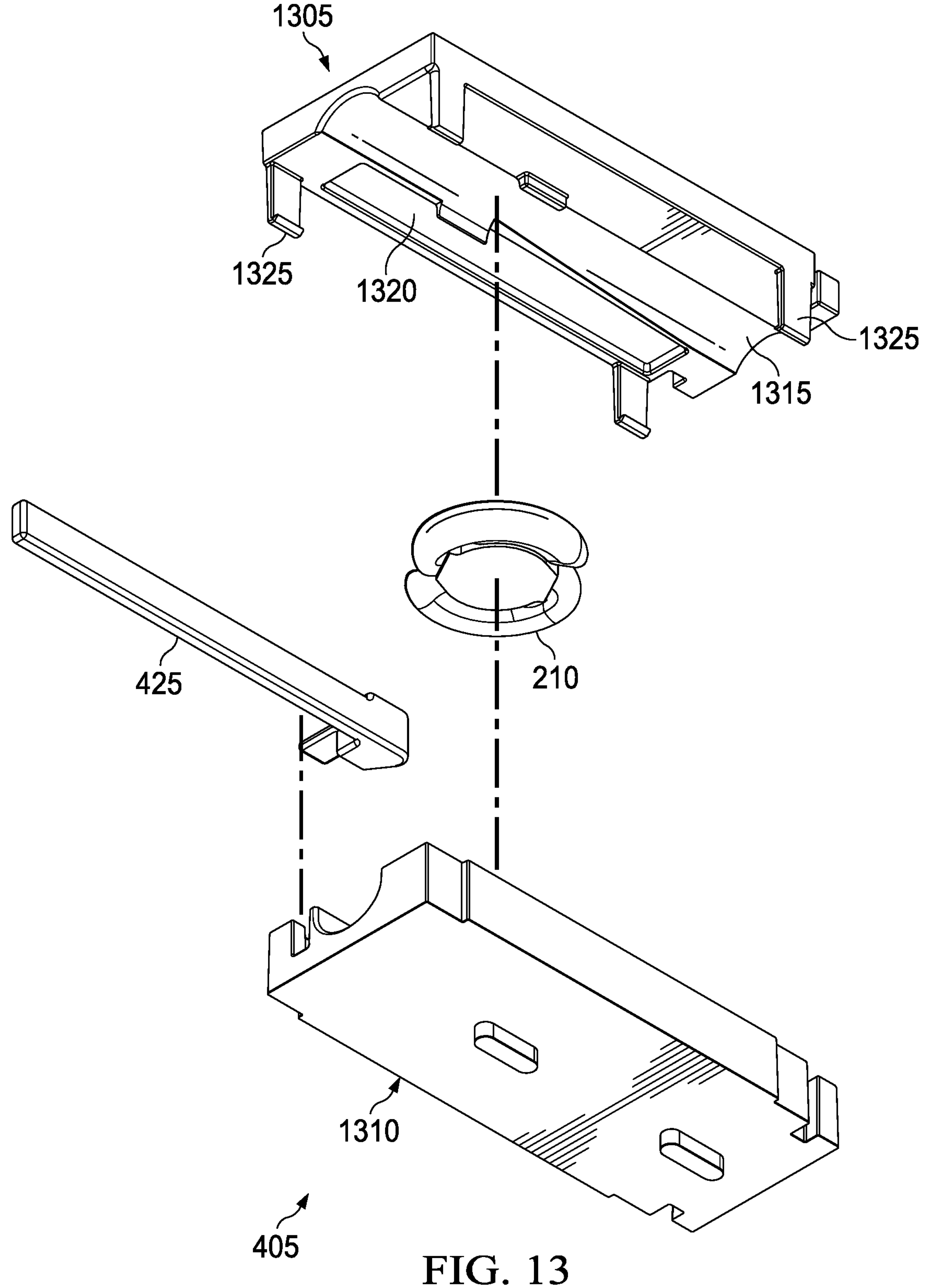
FIG. 13 is an assembly view of an implant management system illustrated in FIG. 4.

FIG. 13 is an assembly view of the implant management system 405 of FIG. 4, illustrating additional details that may be associated with some examples. As illustrated in the example of FIG. 13, the implant 210 and the leading splay arm 425 may be disposed between a lid 1305 and a base 1310. The lid 1305 may additionally comprise a through channel 1315 and a guide channel 1320. The lid 1305 and the base 1310 may be configured to be coupled together to enclose the implant 210 and the leading splay arm 425. For example, the lid 1305 may comprise one or more locking tabs 1325 configured to snap on to the base 1310. In some embodiments, one or more of the lid 1305 and the base 1310 may be transparent to allow the implant 210 to be visible.

Figure 14:
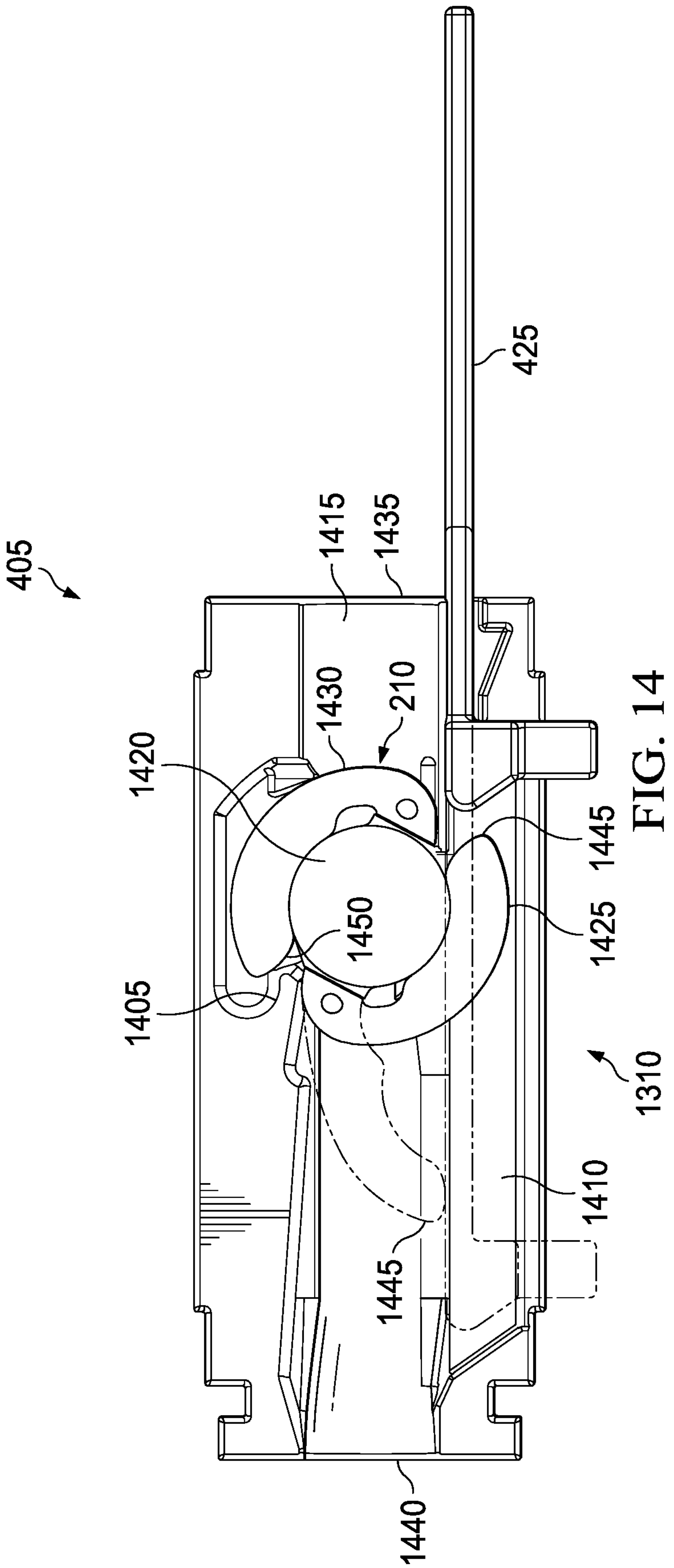
FIG. 14 is a top view of the implant management system of FIG. 13.

FIG. 14 is a top view of the implant management system 405 of FIG. 13, with the lid 1305 removed to further illustrate the implant 210, the leading splay arm 425, and the base 1310. As illustrated in the example of FIG. 14, some embodiments of implant management system 405 may comprise a trailing splay arm 1405, a guide channel 1410, and a through channel 1415. The implant 210 of FIG. 14 comprises an optic body 1420, a leading haptic 1425, and a trailing haptic 1430.

The guide channel 1410 may be configured to align with the guide channel 1320 (see FIG. 13) to constrain the leading splay arm 425 to a linear motion generally parallel to the through channel 1415. The through channel 1415 may be configured to align with the through channel 1315 (see FIG. 13) to form the implant chamber 905 (see, e.g., FIG. 9), which can constrain the optic body 1420 to a linear motion between a plunger port 1435 and a delivery port 1440.

The leading splay arm 425 of FIG. 14 is movable to splay the leading haptic within an implant bay. For example, the leading splay arm 425 of FIG. 14 can be configured to engage a free end 1445 of the leading haptic 1425, and advancing the leading splay arm 425 toward the delivery port 1440 can actively splay the leading haptic 1425 toward the delivery port 1440. In the example of FIG. 14, the leading splay arm 425 comprises a rounded end to facilitate engagement with the free end 1445 of the leading haptic 1425. In other examples, the leading splay arm 425 may comprise other configurations for engaging the free end 1445, such as tapered end or a notched end. In some embodiments, the leading haptic 1425 may be moved into a straight configuration before the optic body 1420 is advanced. The leading splay arm 425 may additionally form a wall along the through channel 1415 as it is advanced toward the delivery port 1440, which can help prevent rotation of the optic body 1420 and maintain alignment of the implant 210.

In the example of FIG. 14, the trailing splay arm 1405 is configured as a substantially rigid extension fixed to the base 1310. The trailing splay arm 1405 may be configured to engage a free end 1450 of the trailing haptic 1430, which can passively splay the trailing haptic 1430 as the optic body 1420 is advanced toward the delivery port 1440. In some examples, the trailing haptic 1430 may be moved into a straight configuration before the optic body 1420 is advanced through the delivery port 1440.

Figure 15:
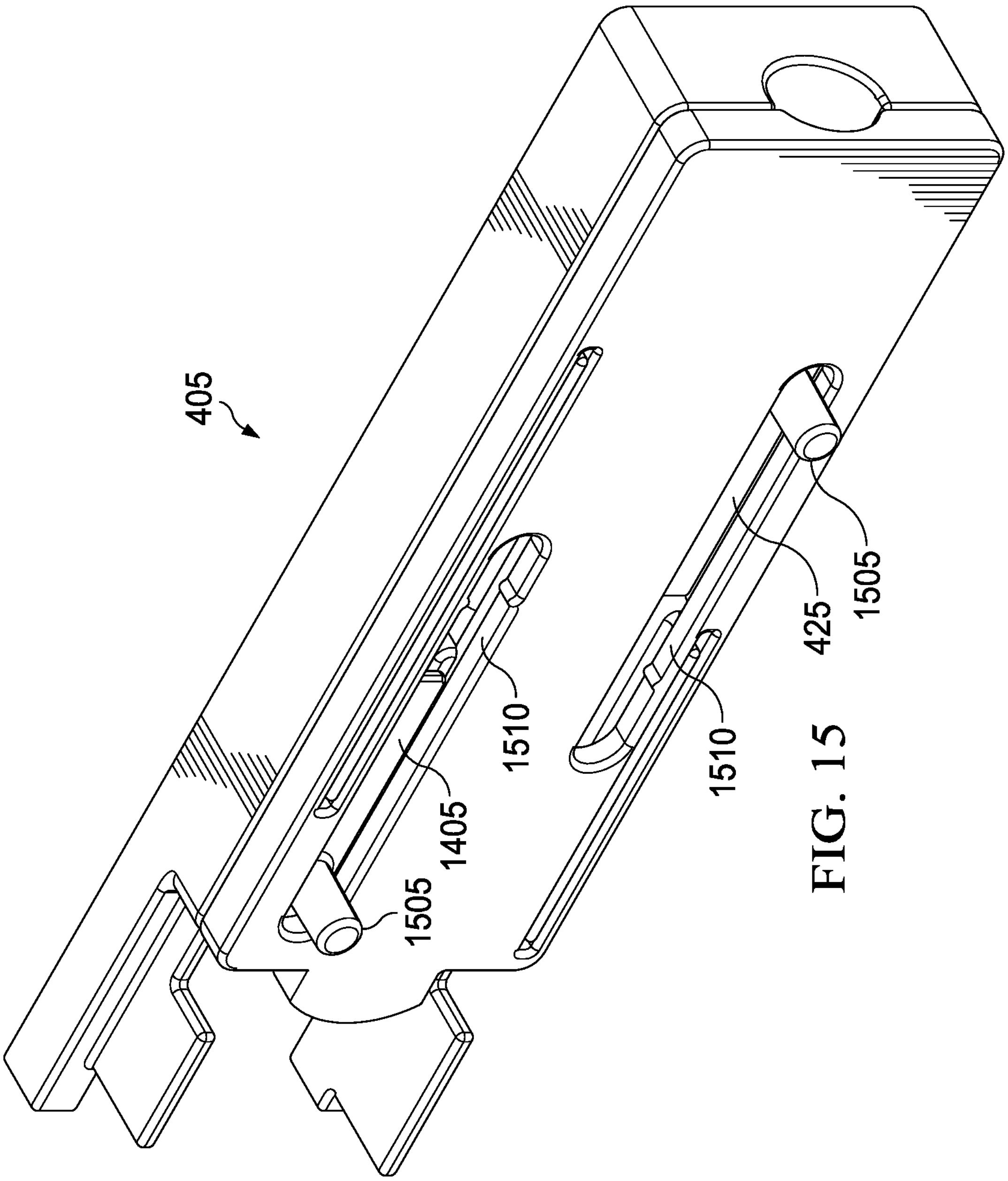
FIG. 15 is an isometric view of another example of an implant management system.

FIG. 15 is an isometric view of another example of the implant management system 405, illustrating additional details that may be associated with some embodiments. For example, as illustrated in FIG. 15, each of the leading splay arm 425 and the trailing splay arm 1405 may comprise at least one actuator 1505. Each of the actuators 1505 are configured to be accessible through a guide track 1510, which is configured to constrain the motion of the actuators 1505 to substantially linear motion. As illustrated in the example of FIG. 15, the guide tracks 1510 may be mutually parallel.

Figure 16:
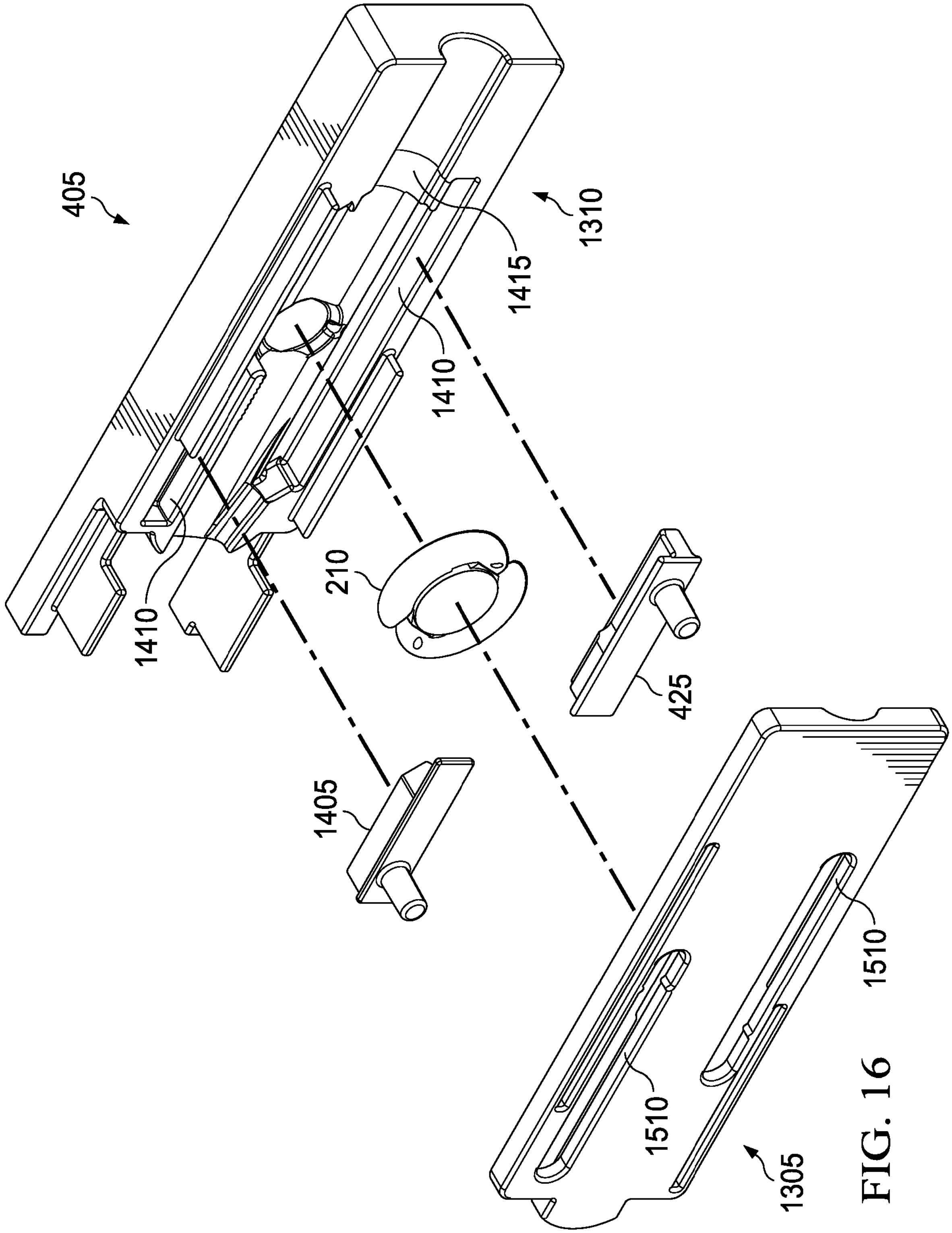
FIG. 16 is an assembly view of the implant management system of FIG. 15.

FIG. 16 is an assembly view of the implant management system 405 of FIG. 15. As illustrated in the example of FIG. 16, the implant 210, the leading splay arm 425, and the trailing splay arm 1405 may be disposed between the lid 1305 and the base 1310. The guide tracks 1510 may be disposed in the lid 1305 in some embodiments. The base 1310 may additionally include one or more guide channels 1410, which may be configured to align with the guide tracks 1510 to constrain the leading splay arm 425 and the trailing splay arm 1405 to substantially linear motion parallel to the through channel 1415.

Figure 17:
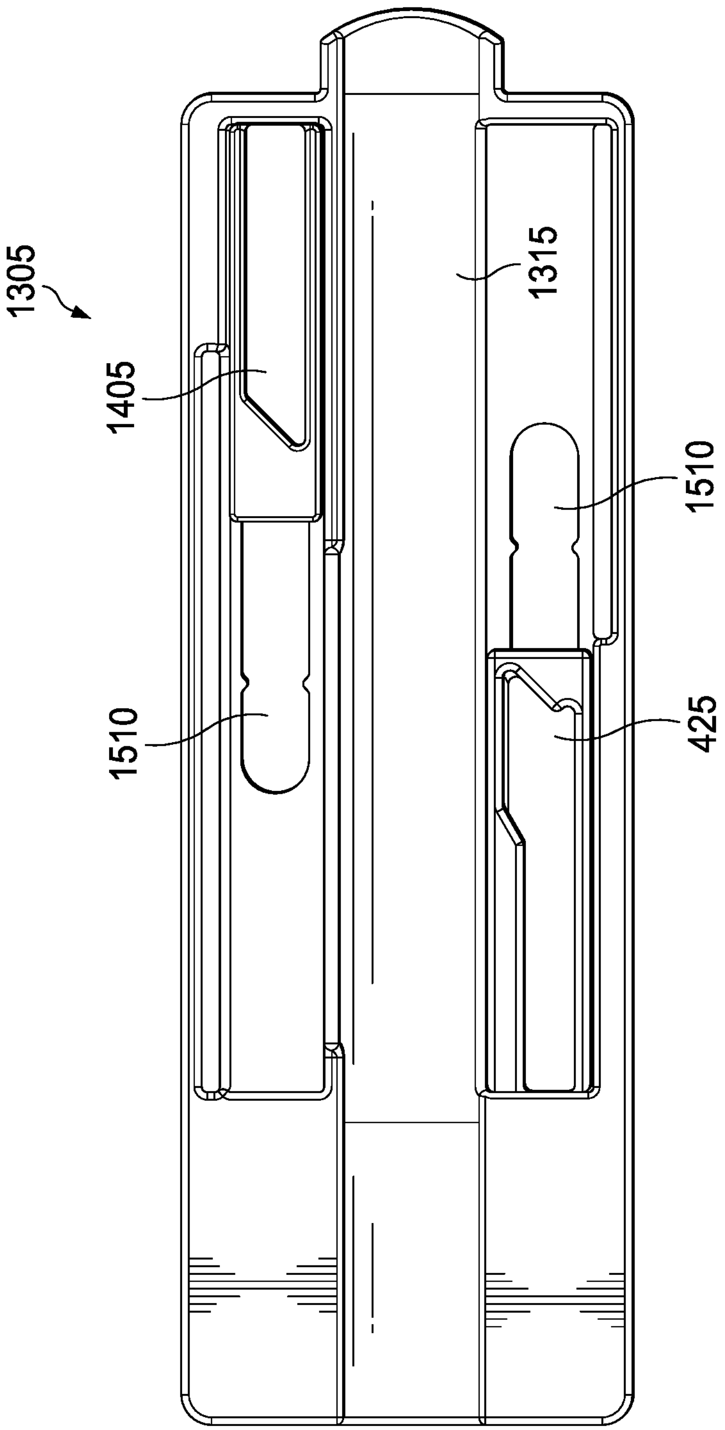
FIG. 17 is a bottom view of a base of that may be associated with some embodiments of the implant management system of FIG. 16.

FIG. 17 is a bottom view of the lid 1305 of FIG. 16, illustrating additional details that may be associated with some embodiments. For example, as illustrated in FIG. 17, the guide tracks 1510 may be mutually parallel and parallel to the through channel 1315. The leading splay arm 425 and the trailing splay arm 1405 may be slidingly received within the guide tracks 1510 and operable to move linearly within the respective guide tracks 1510. The leading splay arm 425 of FIG. 17 comprises a notched end, and the trailing splay arm 1405 comprises a tapered end. In other examples, one or both of the trailing splay arm 1405 and the trailing splay arm may comprise other configurations, such as tapered ends, notched ends, curved ends, or combinations thereof.

Figure 18:
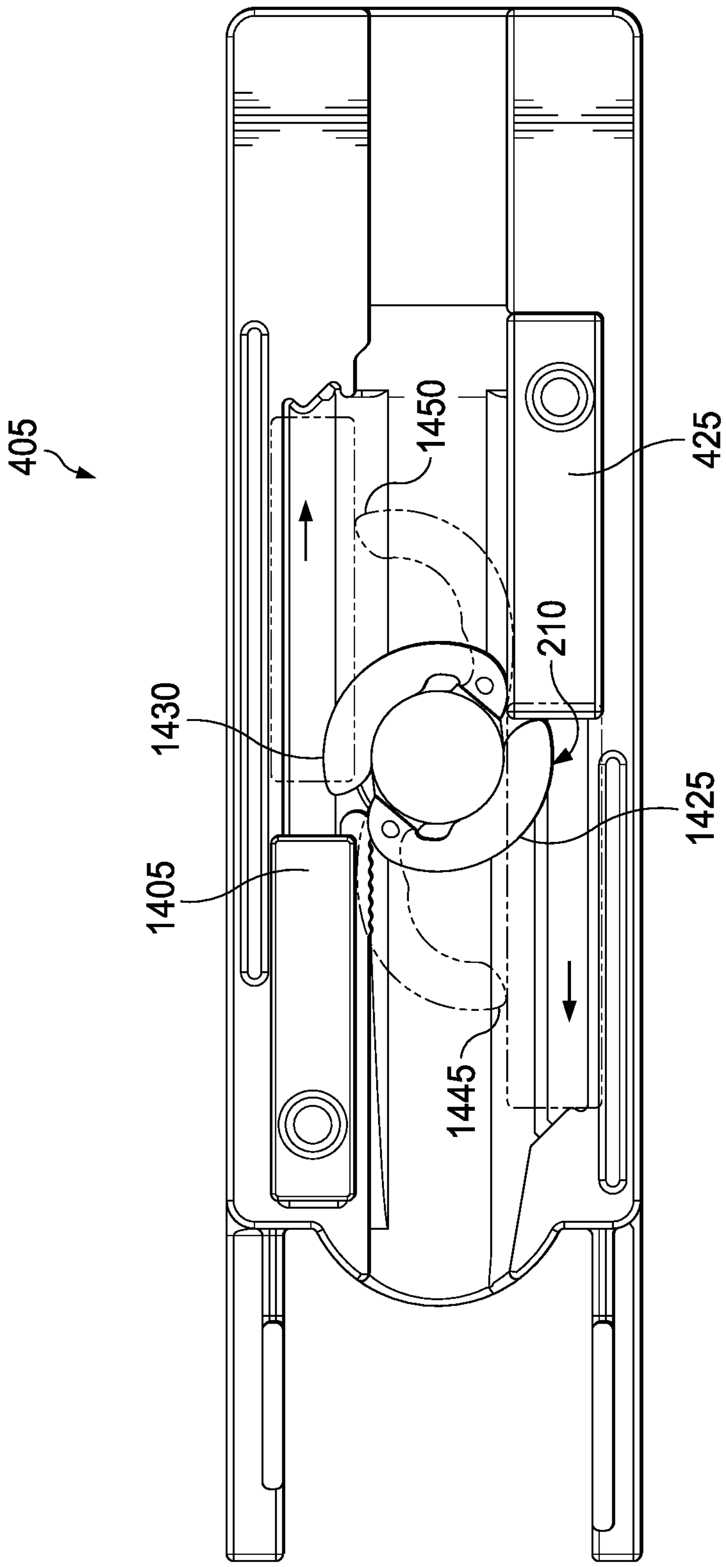
FIG. 18 is a top view of the implant management system of FIG. 15.

FIG. 18 is a top view of the implant management system 405 of FIG. 15 with the lid 1305 removed to further illustrate the implant 210. As illustrated in the example of FIG. 18, the leading splay arm 425 and the trailing splay arm 1405 may be operable to move in opposite directions to splay the leading haptic 1425 and the trailing haptic 1430, respectively. More particularly, in the example of FIG. 18, the leading splay arm 425 is operable to move the free end 1445 of the leading haptic 1425 toward the delivery port 1440, and the trailing splay arm 1405 is operable to move a free end 1450 of the trailing haptic 1430 away from the delivery port 1440. Additionally, in some embodiments, the leading splay arm 425 and the trailing splay arm 1405 may form walls adjacent to the optic body 1420 after splaying the leading haptic 1425 and the trailing haptic 1430, which can help prevent rotation of the optic body 1420 and maintain alignment of the implant 210.

Figure 19:
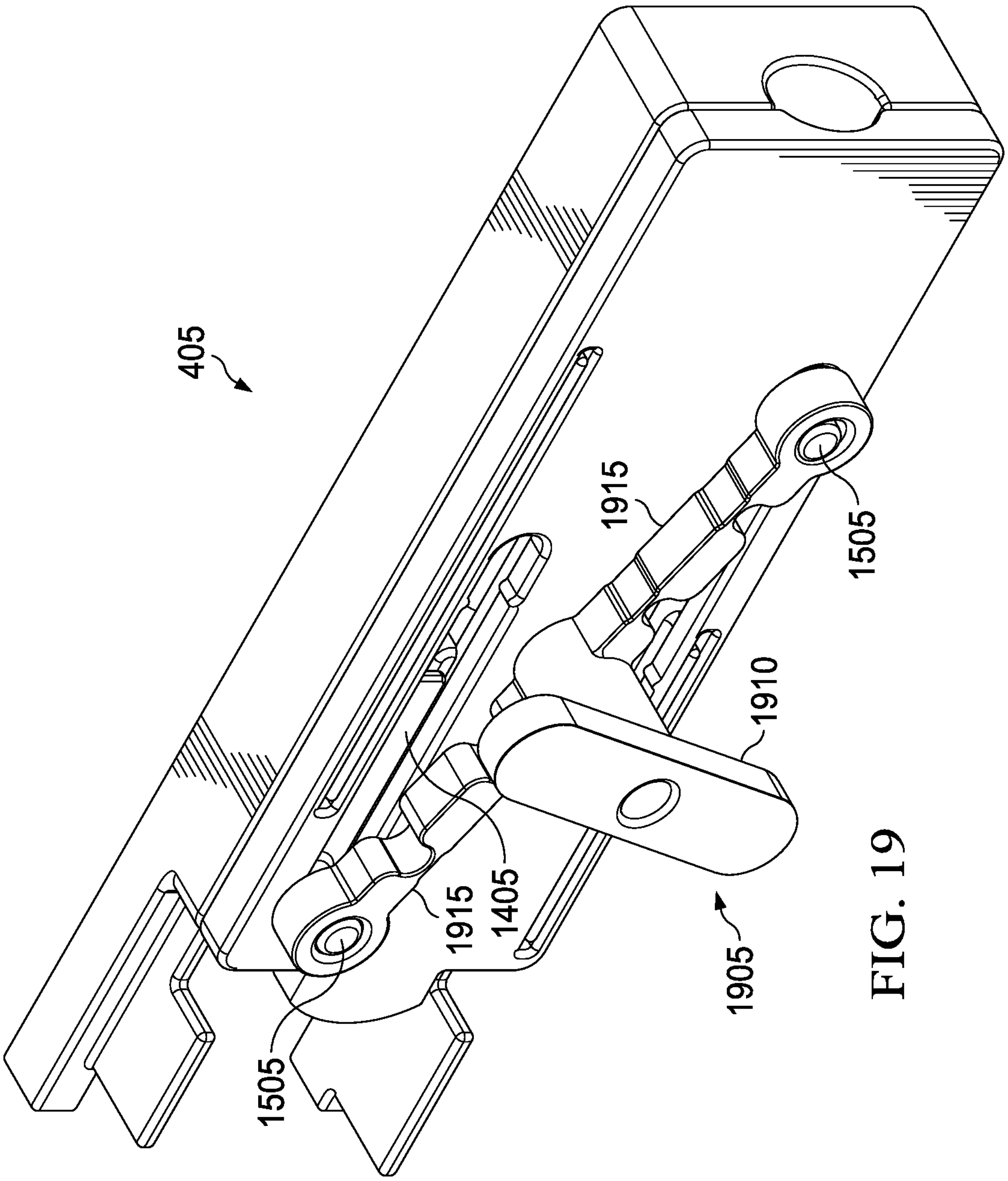
FIG. 19 is an isometric view of another example of an implant management system.

FIG. 19 is an isometric view of another example of the implant management system 405, illustrating additional details that may be associated with some embodiments. For example, the implant management system 405 of FIG. 19 is substantially similar to the implant management system 405 of FIG. 15, further comprising a cam 1905 configured to translate the leading splay arm 425 and the trailing splay arm 1405. For example, the cam 1905 may comprise a dial 1910 and two connector arms 1915, which can be coupled to the actuators 1505. In some embodiments, the cam 1905 may translate the leading splay arm 425 (not visible) and the trailing splay arm 1405 simultaneously.

Figure 20:
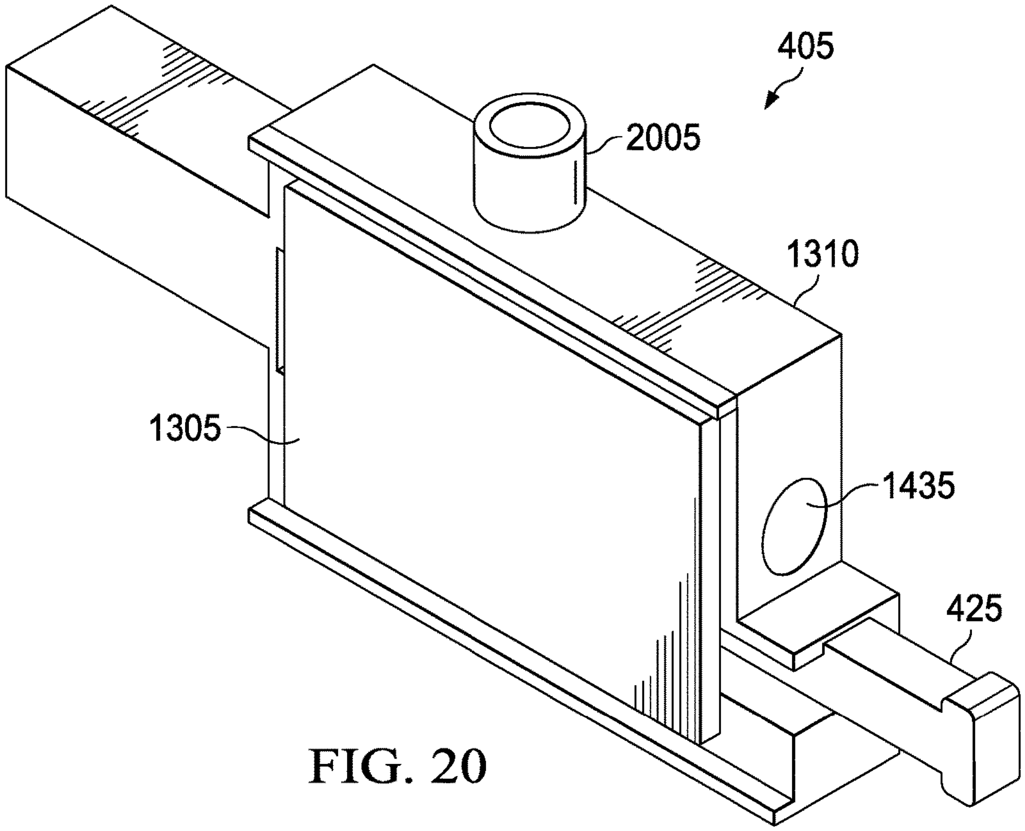
FIG. 20 is an isometric view of another example of the implant management system.

FIG. 20 is an isometric view of another example of the implant management system 405, illustrating additional details that may be associated with some embodiments. As illustrated in the example of FIG. 20, the leading splay arm 425 may be disposed between the lid 1305 and the base 1310, adjacent to the plunger port 1435. FIG. 20 also illustrates an example of a fluid port 2005 that may be associated with some embodiments of the implant management system 405.

Figure 21:
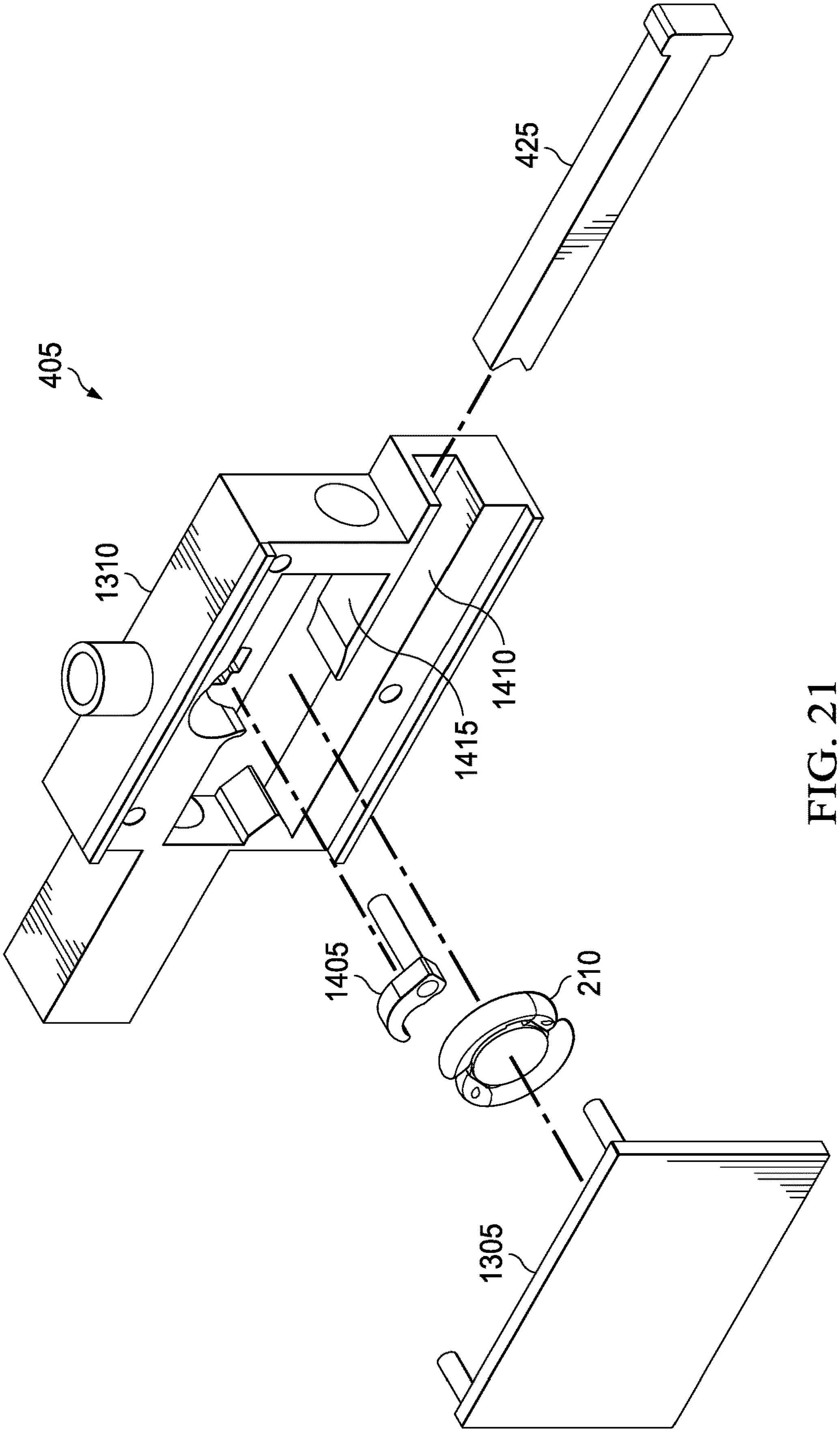
FIG. 21 is an assembly view of the implant management system of FIG. 20.

FIG. 21 is an assembly view of the implant management system 405 of FIG. 20. As illustrated in the example of FIG. 21, the implant 210, the leading splay arm 425, and the trailing splay arm 1405 may be disposed between the lid 1305 and the base 1310. The base 1310 may additionally include one or more guide channels 1410, which may be configured to constrain the leading splay arm 425 to substantially linear motion parallel to the through channel 1415.

Figure 22:
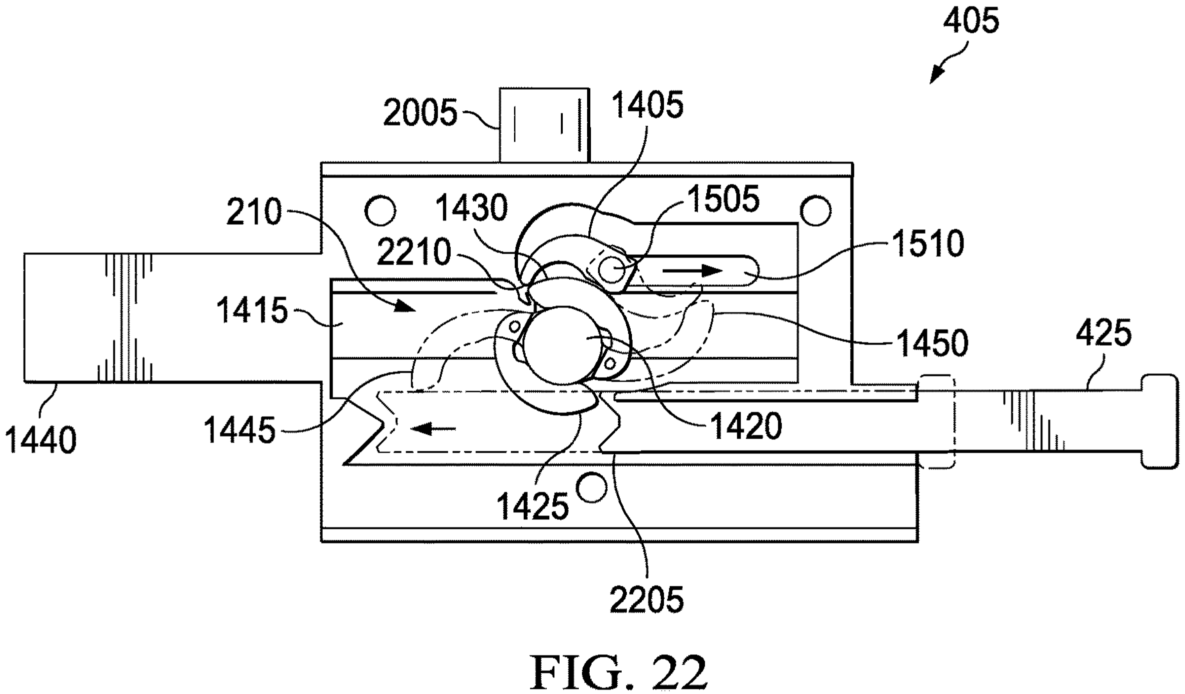
FIG. 22 is a top view of the implant management system of FIG. 21.

FIG. 22 is a top view of the implant management system 405 of FIG. 21 with the lid 1305 removed to further illustrate the implant 210. As illustrated in the example of FIG. 22, the leading splay arm 425 and the trailing splay arm 1405 may be operable to move in opposite directions to splay the leading haptic 1425 and the trailing haptic 1430, respectively. The implant management system 405 of FIG. 22 comprises a guide track 1510, and the actuator 1505 may be configured to move within the guide track 1510 to constrain the actuator 1505 to linear motion parallel to the through channel 1415. More particularly, in the example of FIG. 22, the leading splay arm 425 is operable to move the free end 1445 of the leading haptic 1425 toward the delivery port 1440, and the trailing splay arm 1405 is operable to move the free end 1450 of the trailing haptic 1430 away from the delivery port 1440. In the example of FIG. 22, the leading splay arm 425 comprises a notched end 2205, which can facilitate engagement with the free end 1445, and the trailing splay arm 1405 comprises a curved end 2210, which can facilitate engagement with the free end 1450. Additionally, in some embodiments, at least one of the leading splay arm 425 and the trailing splay arm 1405 may form a wall adjacent to the optic body 1420 after splaying the leading haptic 1425 and the trailing haptic 1430, which can help prevent rotation of the optic body 1420 and maintain alignment of the implant 210. In some examples, the fluid port 2005 may be fluidly coupled to the through channel 1415.

Figure 23:
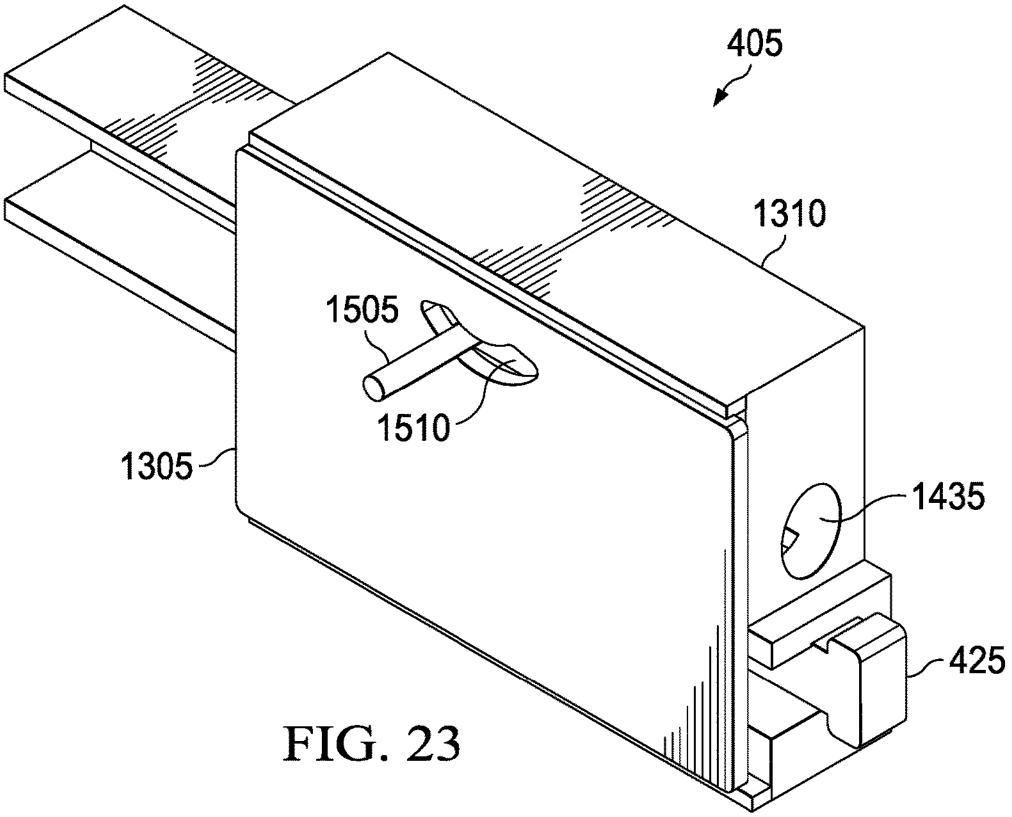
FIG. 23 is an isometric view of another example of an implant management system.

FIG. 23 is an isometric view of another example of the implant management system 405, illustrating additional details that may be associated with some embodiments. The implant management system 405 of FIG. 23 may be similar to the implant management system 405 of FIG. 20 in many respects. The leading splay arm 425 of FIG. 23 may be disposed between the lid 1305 and the base 1310, adjacent to the plunger port 1435. As illustrated in FIG. 23, some embodiments of the actuator 1505 may be constrained by a guide track 1510 in the base 1310. Additionally, or alternatively, the guide track 1510 may be curved in some examples.

Figure 24:
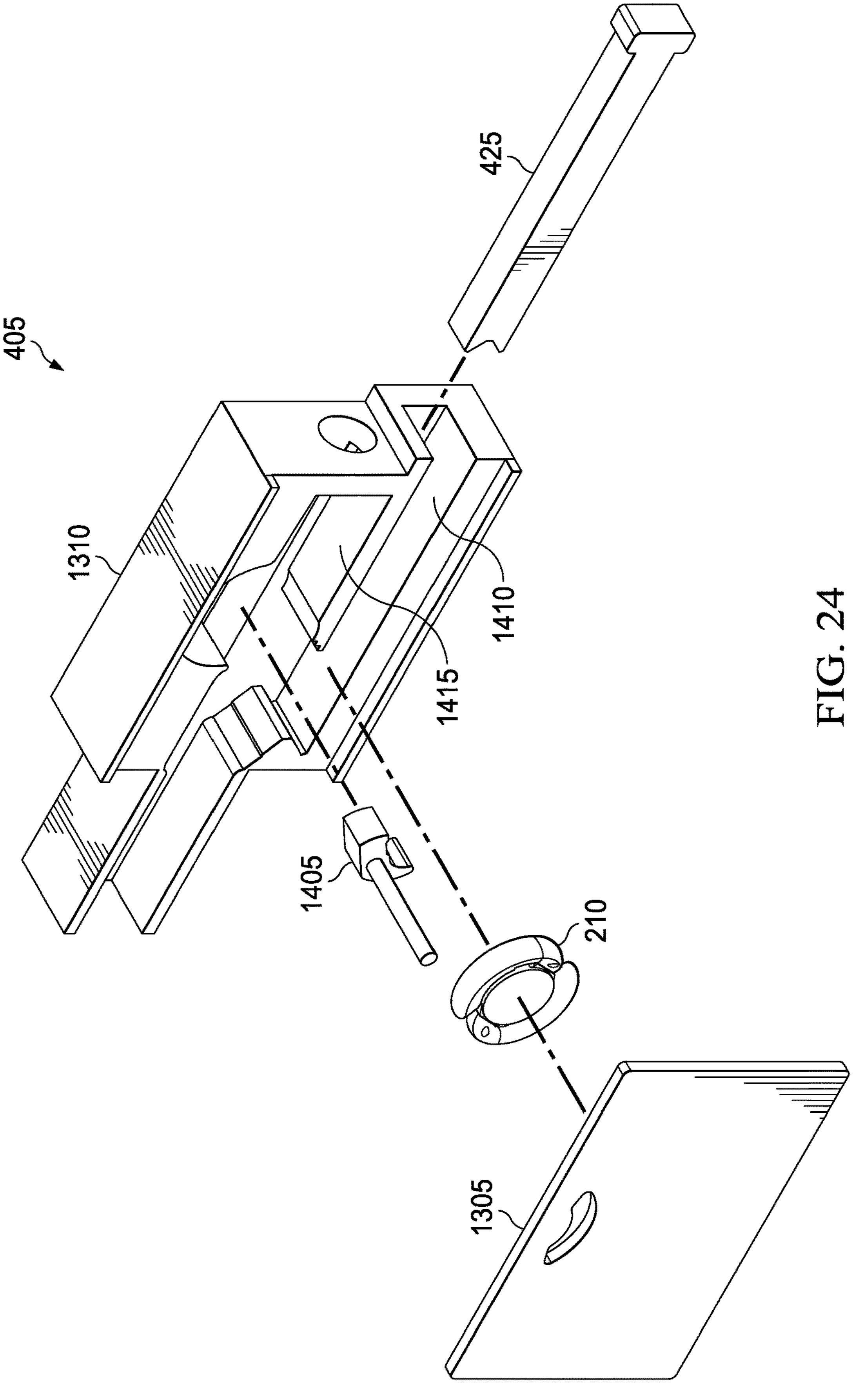
FIG. 24 is an assembly view of the implant management system of FIG. 23.

FIG. 24 is an assembly view of the implant management system 405 of FIG. 23. As illustrated in the example of FIG. 24, the implant 210, the leading splay arm 425, and the trailing splay arm 1405 may be disposed between the lid 1305 and the base 1310. The base 1310 may additionally include a guide channel 1410, which may be configured to constrain the leading splay arm 425 to substantially linear motion parallel to the through channel 1415.

Figure 25:
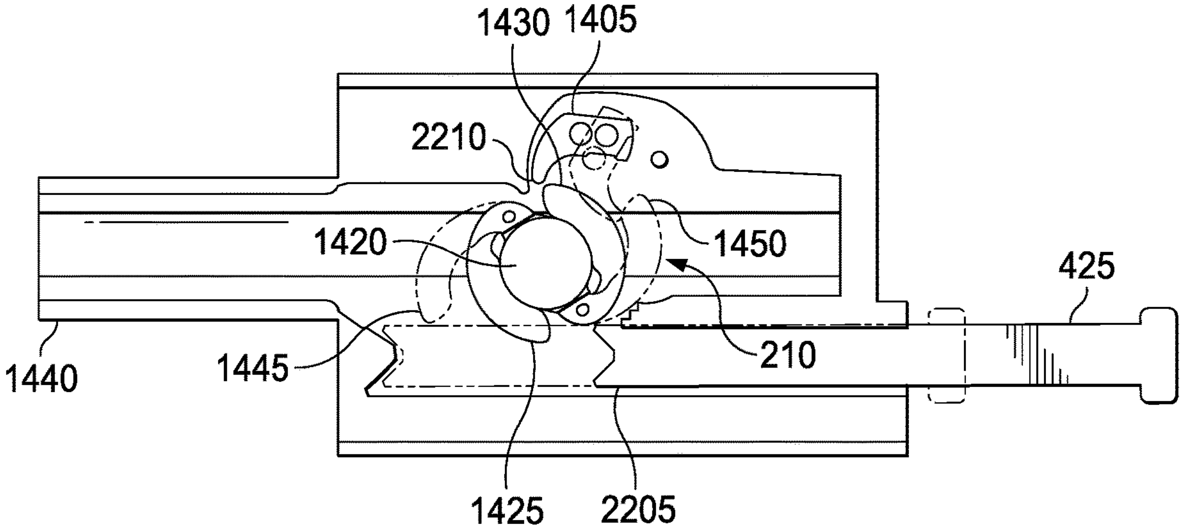
FIG. 25 is a top view of the implant management system of FIG. 23.

FIG. 25 is a top view of the implant management system 405 of FIG. 23 with the lid 1305 removed to further illustrate additional features. As illustrated in the example of FIG. 25, the leading splay arm 425 and the trailing splay arm 1405 may be operable to splay the leading haptic 1425 and the trailing haptic 1430 in opposite directions. More particularly, in the example of FIG. 25, the leading splay arm 425 is operable to move the free end 1445 of the leading haptic 1425 toward the delivery port 1440, and the trailing splay arm 1405 is operable to move the free end 1450 of the trailing haptic 1430 away from the delivery port 1440. In the example of FIG. 25, the leading splay arm 425 comprises a notched end 2205, which can facilitate engagement with the free end 1445, and the trailing splay arm 1405 comprises a curved end 2210, which can facilitate engagement with the free end 1450. Additionally, in some embodiments, at least one of the leading splay arm 425 and the trailing splay arm 1405 may form a wall adjacent to the optic body 1420 after splaying the leading haptic 1425 and the trailing haptic 1430, which can help prevent rotation of the optic body 1420 and maintain alignment of the implant 210.

Figure 26A:
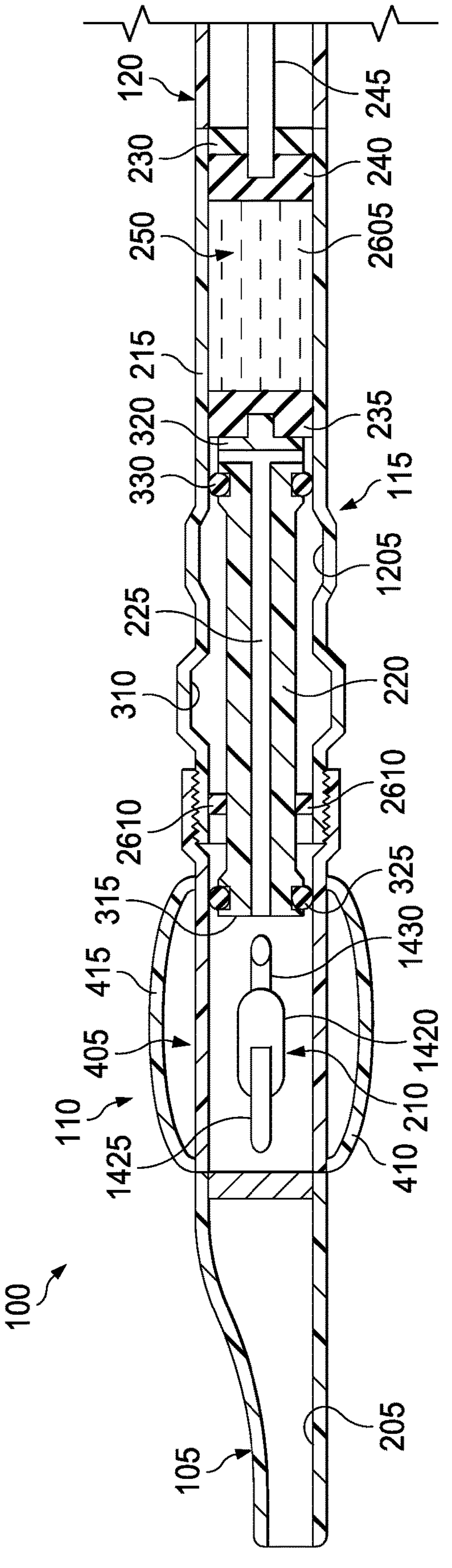
FIGS. 26A-26D are schematic diagrams illustrating an example method of ejecting an implant from the system of FIG. 1.

FIGS. 26A-26D are schematic diagrams illustrating an example method of ejecting the implant 210 from the system 100. Initially, various components of the system 100 may be assembled if needed. For example, the nozzle 105, the implant bay 110, and the actuator 115 may be coupled to each other as illustrated in FIG. 26A. The drive system 120 may also be coupled to the actuator 115 through the drive interface 230. For example, the push rod 245 may engage the drive seal 240 through the drive interface 230 as illustrated in FIG. 26A.

The implant 210 may be provided in the implant management system 405 of the implant bay 110, as illustrated in the example of FIG. 26A. In some embodiments, the implant 210 may comprise an intraocular lens, which may have a shape similar to that of a natural lens of an eye, and it may be made from numerous materials. Examples of suitable materials may include silicone, acrylic, and combinations of such suitable materials. In some instances, the implant 210 may comprise an intraocular lens that is fluid-filled, such as a fluid-filled accommodating intraocular lens.

In some examples, a working fluid 2605 may be stored in the fluid chamber 250. In other examples, such as the embodiment of FIG. 10, the working fluid 2605 may be added to the fluid chamber 250 at any time before use.

Figure 26B:
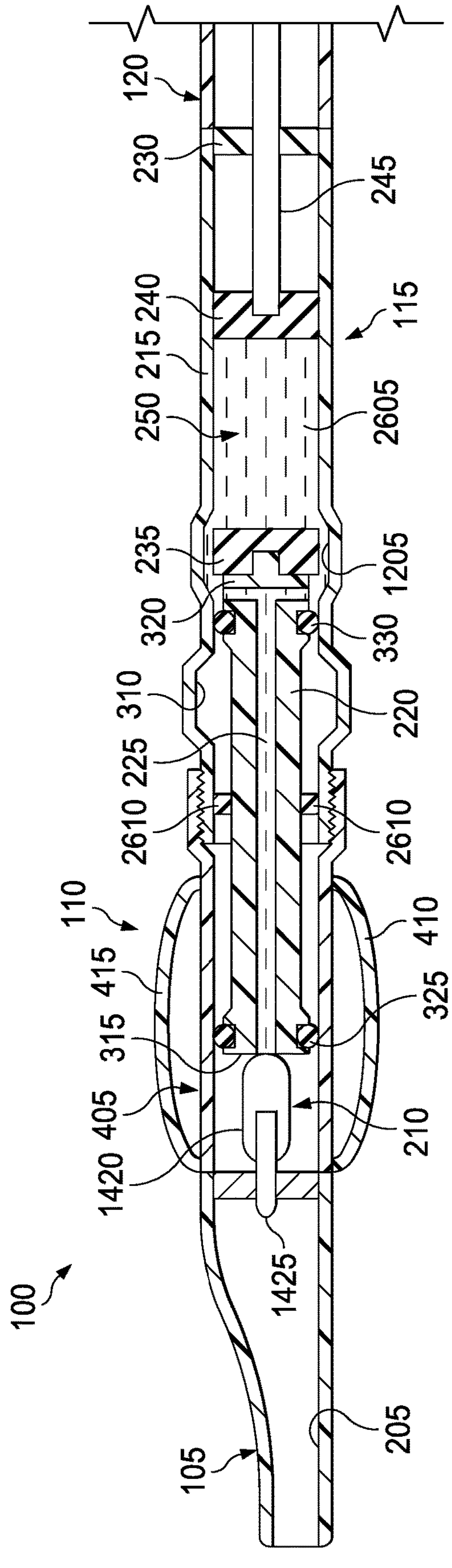
Figure 26C:
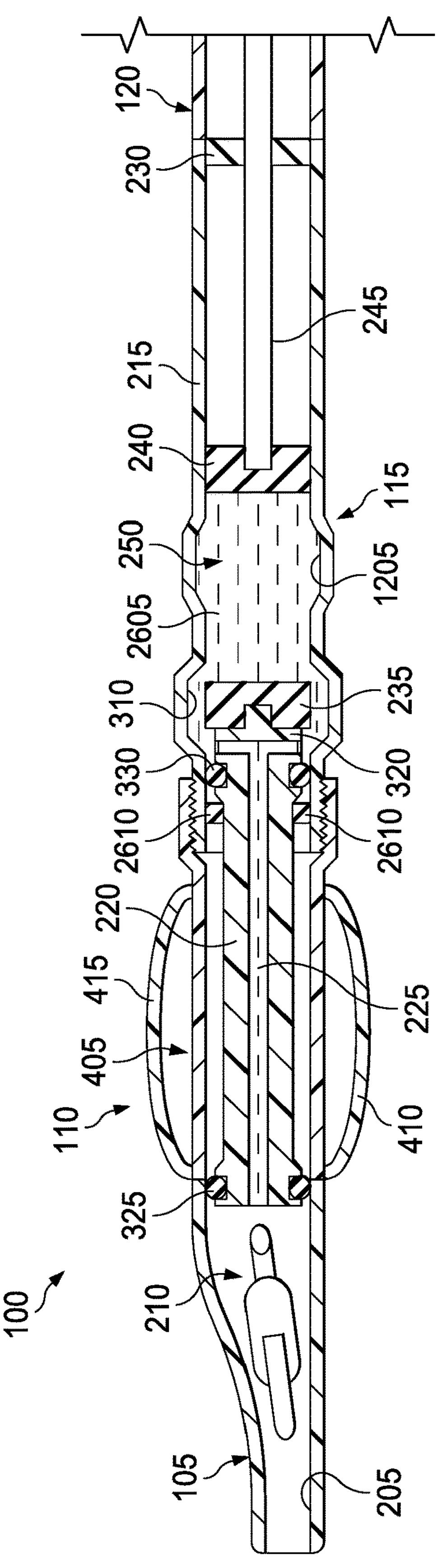
Figure 26D:
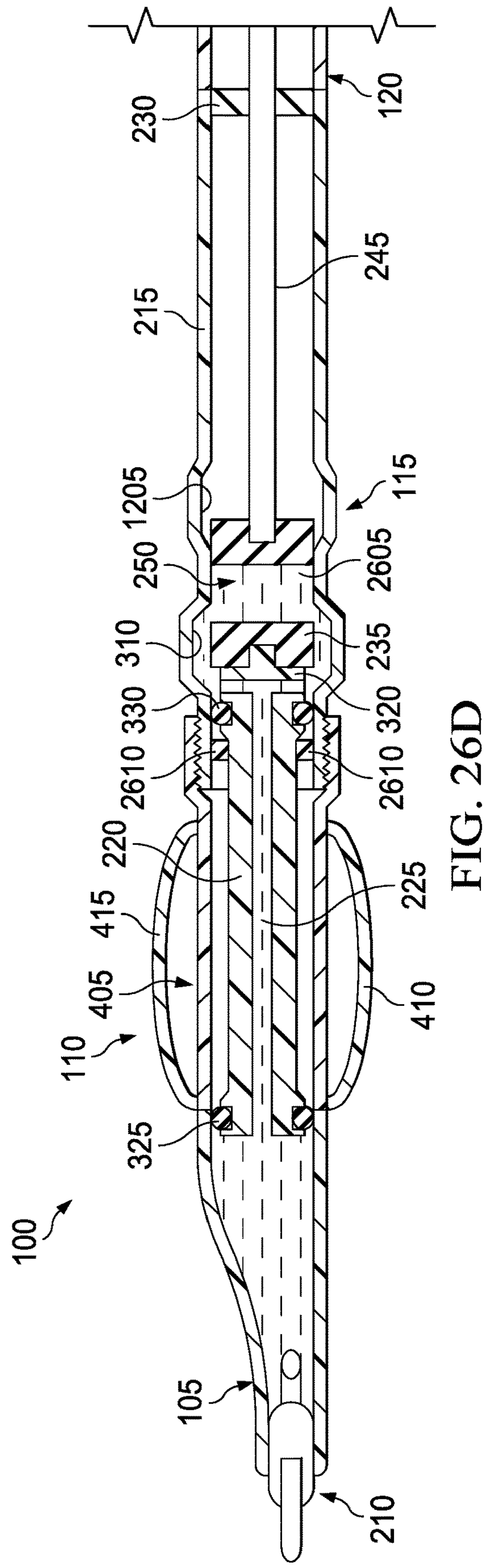

The plunger 220, the plunger seal 235, and the drive seal 240 are generally movable within the housing between a first position, as illustrated in the example of FIG. 26A, and other positions illustrated in FIG. 26B-26D.

In the first position of FIG. 26A, the plunger seal 235 fluidly isolates the bore 225 from the working fluid 2605 in the fluid chamber 250, which can allow the working fluid 2605 to be stored within the fluid chamber 250 in the first position. In some examples, the nozzle seal 325 and the first end 315 of the plunger 220 may protrude into the implant bay 110 in the first position, as illustrated in FIG. 26A, which can create a seal in the implant bay 110 behind the implant 210. The first end 315 of the plunger 220 may also engage the implant 210 in the first position, in some examples. In other examples, the nozzle seal 325 and the first end 315 may be contained within the housing 215 in the first position.

In some embodiments, the implant management system 405 may be actuated to configure the implant 210 for delivery. For example, the implant management system 405 may straighten one or more of the leading haptic 1425 and the trailing haptic 1430. In some embodiments, the leading haptic 1425 may be actively splayed and the trailing haptic 1430 may be passively splayed, such as in the example of FIG. 14. In other examples, both may be actively splayed, such as in the example of FIG. 18.

In some embodiments, the drive system 120 may move the push rod 245 against the drive seal 240. The plunger 220, the plunger seal 235, the drive seal 240, and the working fluid 2605 can rigidly move to a second position, maintaining a fixed relationship as illustrated in FIG. 26B, in response to the force of the push rod 245 on the drive seal 240. In the example of FIG. 26B, the implant 210 is also advanced partially into the delivery lumen 205 of the nozzle 105 by the first end 315 of the plunger 220. For example, the first end 315 may engage the optic body 1420 in some embodiments. Advancement may also passively straighten the trailing haptic 1430 in some embodiments. In the second position of FIG. 26B, the plunger seal 235 is advanced to a position adjacent to the priming channel 1205. The priming channel 1205 fluidly couples the fluid chamber 250 to the bore 225 around the plunger seal 235. As the push rod 245 and the drive seal 240 apply pressure to the working fluid 2605 in the fluid chamber 250, the working fluid 2605 may move into the bore 225 through the priming channel 1205.

In general, the rate of fluid flow through the priming channel 1205 is sufficiently low and brief to minimize bubble formation in the fluid and to maintain a pressure in the working fluid 2605 sufficient to continue advancement of the plunger seal 235 and the plunger 220 to a third position, as illustrated in FIG. 26C, in response to pressure applied to the drive seal 240 by the push rod 245. In the position of FIG. 26C, the implant 210 is advanced further into the delivery lumen 205, which may create a fluid seal between the implant 210 and the delivery lumen 205. In some examples, the implant 210 may be positioned entirely within the delivery lumen 205. In the third position, the bypass channel 310 fluidly couples the bore 225 to the fluid chamber 250 around the plunger seal 235. As the push rod 245 and the drive seal 240 apply pressure to the working fluid 2605 in the fluid chamber 250, the working fluid 2605 may move into the bore 225 through the bypass channel 310, unimpeded at a higher flow rate.

The plunger 220 may be retained in the third position of FIG. 26C against further force applied to the drive seal 240. For example, in some embodiments, the second end 320 of the plunger 220 may be flared, and the plunger interface 305 may be configured to engage the second end 320 to limit advancement. Additionally, or alternatively, the implant bay 110 or the nozzle 105 may comprise a plunger stop 2610 configured to engage some portion or feature of the plunger 220, such as the second end 320 of the plunger 220, to prevent further advancement. In yet other examples, some embodiments of the delivery lumen 205 may be tapered, which can prevent further advancement of the plunger 220 toward the insertion tip 615. For example, the diameter of the delivery lumen 205 may decrease as it gets closer to the insertion tip 615.

With the plunger 220 retained, additional pressure applied by the drive seal 240 on the working fluid 2605 can move the working fluid 2605 through the bypass channel 310 and the bore 225, as illustrated in the example of FIG. 26D. Movement of the working fluid 2605 from the bore 225 into the delivery lumen 205 under pressure from the drive seal 240 can increase the pressure and flow rate of the working fluid 2605 in the delivery lumen 205 behind the implant 210, which can advance the implant 210 further through the delivery lumen 205 until the implant 210 is ejected.

Figure 27A:
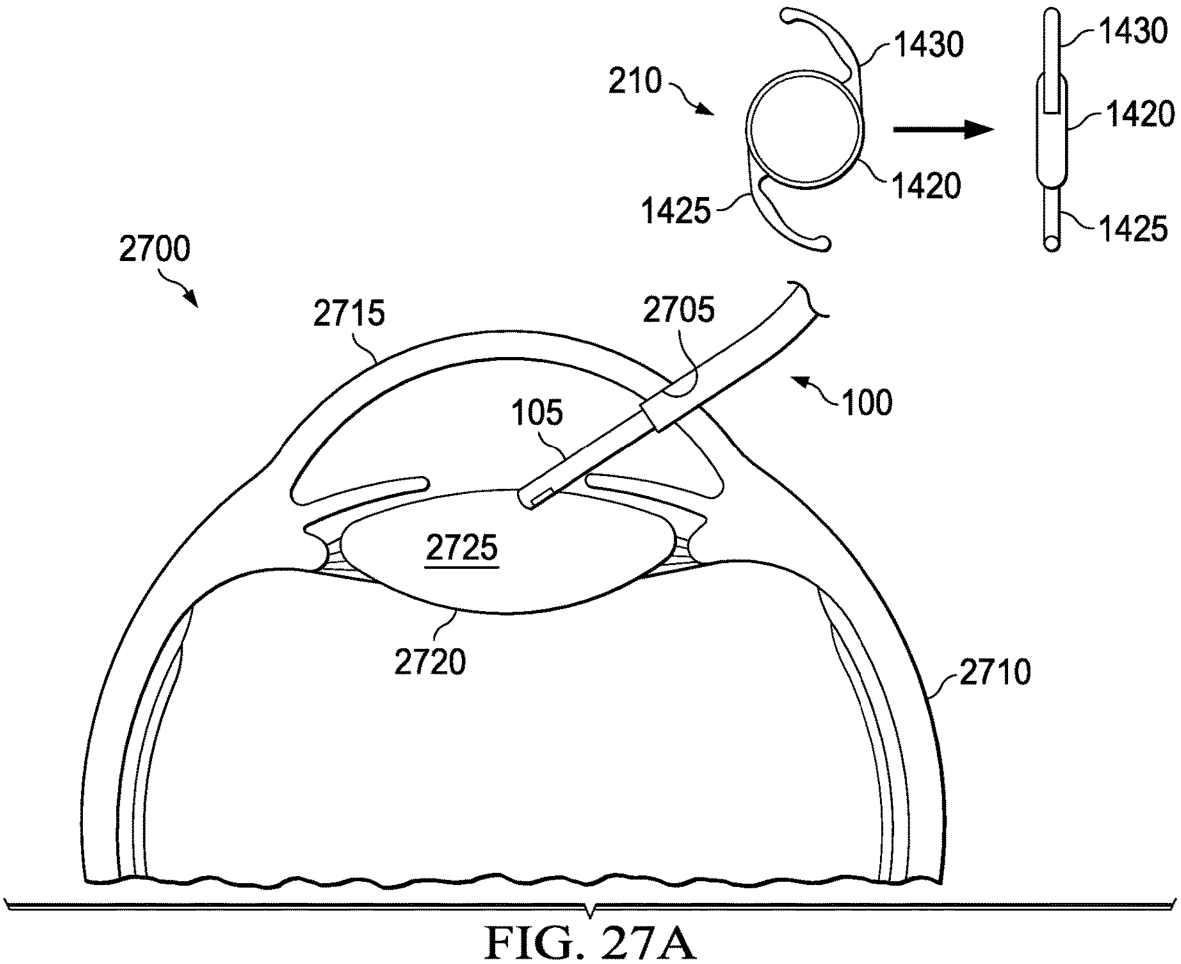
FIG. 27A-27B are schematic diagrams illustrating an example application of the system of FIG. 1 to insert an implant into an eye.
Figure 27B:
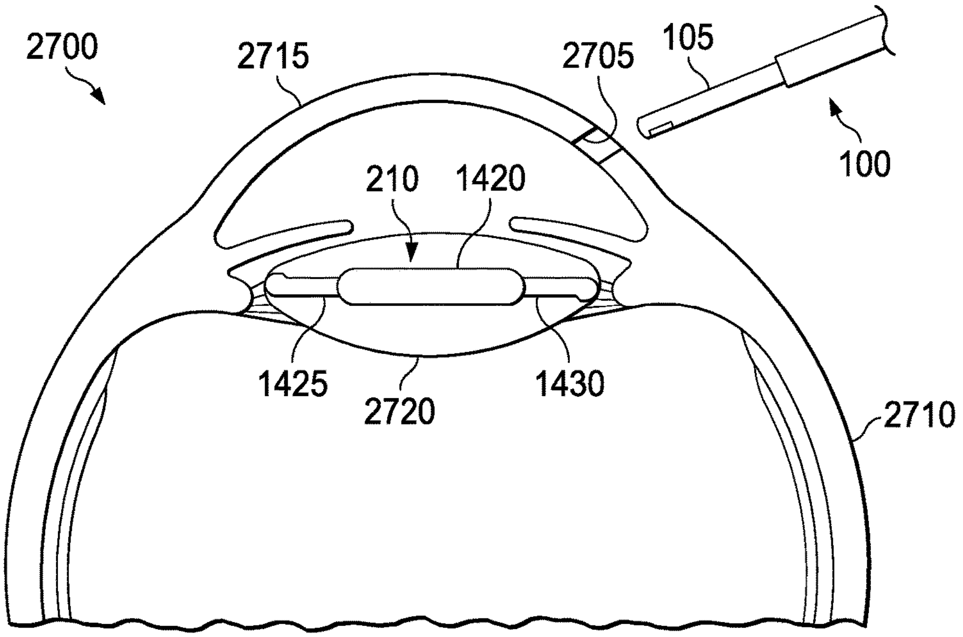

FIGS. 27A-27B are schematic diagrams further illustrating an example use of the system 100 to deliver the implant 210 to an eye 2700. As illustrated, an incision 2705 may be made in the eye 2700 by a surgeon, for example. In some instances, the incision 2705 may be made through the sclera 2710 of the eye 2700. In other instances, an incision may be formed in the cornea 2715 of the eye 2700. The incision 2705 may be sized to permit insertion of a portion of the nozzle 105 in order to deliver the implant 210 into the capsular bag 2720. For example, in some instances, the size of the incision 2705 may have a length less than about 3000 microns (3 millimeters). In other instances, the incision 2705 may have a length of from about 1000 microns to about 1500 microns, from about 1500 microns to about 2000 microns, from about 2000 microns to about 2500 microns, or from about 2500 microns to about 3000 microns.

After the incision 2705 is made, the nozzle 105 can be inserted through the incision 2705 into an interior portion 2725 of the eye 2700. The system 100 can then eject the implant 210 through the nozzle 105 into the capsular bag 2720 of the eye 2700. In the example of FIG. 27B, the implant 210 is illustrative of an intraocular lens having the optic body 1420, the leading haptic 1425, and the trailing haptic 1430. For example, the implant 210 may be in the form of an accommodating intraocular lens having one or more of the optic body 1420, the leading haptic 1425, and the trailing haptic 1430 filled with fluid. In some applications, the implant 210 may be delivered in a straightened configuration, with one or both of the leading haptic 1425 and the trailing haptic 1430 in a splayed configuration, and can revert to an initial, resting state with the leading haptic 1425 and the trailing haptic 1430 being at least partially curved around the optic body 1420, within the capsular bag 2720, as shown in FIG. 27B. The capsular bag 2720 can retain the implant 210 within the eye 2700 in a relationship relative to the eye 2700 so that the optic body 1420 refracts light directed to the retina (not shown). The leading haptic 1425 and the trailing haptic 1430 can engage the capsular bag 2720 to secure the implant 210 therein. After dispensing the implant 210 into the capsular bag 2720, the nozzle 105 may be removed from the eye 2700 through the incision 2705, and the eye 2700 can be allowed to heal over a period of time.

The systems, apparatuses, and methods described herein may provide significant advantages. For example, some embodiments may be particularly advantageous for delivering intraocular lenses, including fluid-filled accommodating lenses, which can present unique challenges for delivery.

Some embodiments can straighten and/or compress a relatively large lens to fit through an acceptably small incision, manage deformation caused by shifting fluid during compression and exit from a nozzle, and execute delivery in a predictable and controlled manner. Additionally, some embodiments can reduce system complexity and the number of delivery steps while maintaining haptic position consistency. Some embodiments may also reduce the amount of working fluid for delivery.

While shown in a few illustrative embodiments, a person having ordinary skill in the art will recognize that the systems, apparatuses, and methods described herein are susceptible to various changes and modifications that fall within the scope of the appended claims. Moreover, descriptions of various alternatives using terms such as “or” do not require mutual exclusivity unless clearly required by the context, and the indefinite articles “a” or “an” do not limit the subject to a single instance unless clearly required by the context. Components may be also be combined or eliminated in various configurations for purposes of sale, manufacture, assembly, or use. For example, in some configurations, the nozzle 105, the implant bay 110, the actuator 115, the drive system 120 may each be separated from one another or combined in various ways for manufacture or sale.

The claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described in the context of some embodiments may also be omitted, combined, or replaced by alternative features serving the same, equivalent, or similar purpose without departing from the scope of the invention defined by the appended claims.

What is claimed is:

1. An apparatus for eye surgery, the apparatus comprising:

a nozzle having a delivery lumen;

an implant bay coupled to the nozzle;

an implant disposed in the implant bay, the implant comprising an optic body, a leading haptic, and a trailing haptic;

an actuator comprising a housing, a plunger disposed within the housing, a fluid chamber, and a bore through the plunger that is fluidly coupled to the delivery lumen; and a leading splay arm operable to splay the leading haptic within the implant bay;

wherein the plunger is moveable from a first position to a second position to advance the optic body from the implant bay to the delivery lumen after the leading splay arm splays the leading haptic; and wherein the bore is fluidly isolated from the fluid chamber in the first position of the plunger and is fluidly coupled to the fluid chamber in the second position of the plunger.

2. The apparatus of claim 1, wherein the implant bay comprises a trailing splay arm operable to passively splay the trailing haptic of the implant as the plunger advances the implant.

3. The apparatus of claim 1, wherein the leading splay arm forms a wall adjacent to the optic body within the implant bay after splaying the leading haptic.

4. The apparatus of claim 1, wherein:

the implant bay further comprises a trailing splay arm; and the trailing splay arm is operable to splay a trailing haptic of the implant.

5. The apparatus of claim 4, wherein:

the leading splay arm comprises a leading notched end; and the trailing splay arm comprises a trailing notched end.

6. The apparatus of claim 4, wherein:

the leading splay arm comprises a notched end; and the trailing splay arm comprises a curved end.

7. The apparatus of claim 4, wherein the leading splay arm and the trailing splay arm are operable to move in opposite directions.

8. The apparatus of claim 4, wherein:

the leading splay arm is operable to move a free end of the leading haptic toward the delivery lumen; and the trailing splay arm is operable to move a free end of the trailing haptic away from the delivery lumen.

9. The apparatus of claim 1, wherein:

the actuator further comprises a bypass channel; and the bore is fluidly coupled to the fluid chamber through the bypass channel in the second position.

10. The apparatus of claim 9, wherein the actuator is configured to move fluid from the fluid chamber to the delivery lumen through the bypass channel and the bore in the second position.

11. The apparatus of claim 9, wherein the actuator further comprises a drive seal configured to move fluid from the fluid chamber through the bypass channel and the bore in the second position.

12. The apparatus of claim 9, wherein the actuator further comprises a priming channel configured to fluidly couple the bore to the fluid chamber between the first position and the second position.

13. The apparatus of claim 12, wherein:

the bypass channel has a first flow rate;

the priming channel as a second flow rate; and the second flow rate is less than the first flow rate.

14. An apparatus for eye surgery, the apparatus comprising:

a delivery lumen;

an implant chamber;

an implant disposed in the implant chamber, the implant comprising an optic body, a leading haptic, and a trailing haptic;

a leading splay arm operable to splay the leading haptic;

a trailing splay arm operable to splay the trailing haptic;

a plunger having a first end, a second end, and a bore between the first end and the second end;

a fluid chamber configured to store a working fluid; and a push rod;

wherein the plunger is movable between a first position and a second position to advance the implant from the implant chamber to the delivery lumen, and the push rod is configured to move the working fluid from the fluid chamber through the bore in the second position to advance the implant through the delivery lumen.

15. The apparatus of claim 14, wherein the leading splay arm forms a wall adjacent to the optic body after splaying the leading haptic.

16. The apparatus of claim 15, wherein the trailing splay arm forms a second wall adjacent to the optic body after splaying the trailing haptic.

17. The apparatus of claim 14, wherein:

the leading splay arm comprises a leading notched end; and the trailing splay arm comprises a trailing notched end.

18. The apparatus of claim 14, wherein:

the leading splay arm comprises a notched end; and the trailing splay arm comprises a curved end.

19. The apparatus of claim 14, wherein the leading splay arm and the trailing splay arm are operable to move in opposite directions.

20. The apparatus of claim 14, wherein:

the implant chamber comprises a delivery port;

the leading splay arm is operable to move a free end of the leading haptic toward the delivery port; and the trailing splay arm is operable to move a free end of the trailing haptic away from the delivery port.

21. The apparatus of claim 14, further comprising a cam configured to translate the leading splay arm and the trailing splay arm.

22. A method of ejecting a lens from a surgical delivery system, the method comprising:

providing the lens in an implant bay;

straightening a leading haptic of the lens with a leading splay arm;

advancing the lens from the implant bay to a delivery lumen with a rigid plunger;

fluidly coupling a fluid chamber to a bore in the rigid plunger through a bypass channel;

pressing fluid in the fluid chamber to move the fluid through bypass channel and the bore to the delivery lumen; and advancing the lens through the delivery lumen with the fluid;

wherein the fluid is a liquid or viscous fluid.

23. The method of claim 22, further comprising straightening a trailing haptic of the lens with a trailing splay channel in the implant bay.

24. The method of claim 22, further comprising straightening a trailing haptic of the lens with a trailing splay arm.

25. The method of claim 22, wherein the leading splay arm straightens the leading haptic toward the delivery lumen.

26. The method of claim 24, wherein the trailing splay arm straightens the trailing haptic away from the delivery lumen.

* * * * *